US006902930B2

(12) United States Patent
Liang

(10) Patent No.: US 6,902,930 B2
(45) Date of Patent: Jun. 7, 2005

(54) HUMAN MOB-5 (IL-24) RECEPTORS AND USES THEREOF

(75) Inventor: Peng Liang, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 99 days.

(21) Appl. No.: 10/233,873

(22) Filed: Aug. 29, 2002

(65) Prior Publication Data

US 2003/0078381 A1 Apr. 24, 2003

Related U.S. Application Data

(60) Provisional application No. 60/315,684, filed on Aug. 29, 2001.

(51) Int. Cl.$^7$ .................. A61K 38/17; C12N 15/63; C12N 5/10; C07K 14/715

(52) U.S. Cl. .................. 435/320.1; 435/325; 514/12; 514/2; 530/350

(58) Field of Search .................. 435/320.1, 325; 514/12, 2; 530/350

(56) References Cited

U.S. PATENT DOCUMENTS 5,422,264 A * 6/1995 Quaranta et al. .......... 435/391
5,945,511 A   8/1999 Lok et al.

FOREIGN PATENT DOCUMENTS

WO   WO 95 11986 A   5/1995
WO   WO 99 64576 A   12/1999

OTHER PUBLICATIONS

DATABASE EMBL Sep. 11, 1997, "Rattus norvegicus c49a mRNA, complete cds" Database accession No. AF004774.
Database Swall Nov. 1, 1999 "C49a" Database accession No. 09WVP8.
DATABASE EMBL Dec. 31, 1995 "Human MDA–7 mRNA, complete cds" Database accession No. U16261.
Database Swall Nov. 1, 1997 "Interleukin–24 precursor (MDA–7)" Database accession No. Q13007.
Dumoutier et al., "Cutting Edge: STAT Activation By IL–19, IL–20 and mda–7 Through IL–20 Receptor Complexes of Two Types." J. of Immunol 167:3545–3549 (2001).
Dumoutier et al., "Human interleukin–10–related T cell– derived inducible factor: Molecular cloning and functional characterization as an hepatype–stimulating factor," Proc. Acad. Sci. USA 97(18):10144–10149 (Aug. 29, 2000).
Hakryul et al. "Cloning oncogenic Ras–regulated genes by differential display," Methods (ORLANDO), 16(4):365–372 (Dec. 1998).
Jiang et al., "The melanoma differentiation associated gene mda–7 suppresses cancer cell growth." Proc. Natl. Acad. Sci. USA 93:9160–9165 (1996).

Jiang et al., "Subtraction hybridization identified a novel melanoma differentiation associated gene, mda–7, modulated during human melanoma differentiation, growth and progression." Oncogene 11:2477–2486 (1995).
Knappe et al., "Induction of a Novel Cellular Homolog of Interleukin–10, AK155, by Transformation of T Lymphocytes with Herpevirus Samimiri." J. Virol. 74(8):3881–3887 (Apr. 2000).
Kotenko et al., "Identification and functional characterization of a second chain of the interleukin–receptor complex." EMBO J 16(18)5894–5903 (1997).
Kotenko and Pestka, Oncogene 19:2557–2565 (2000).
Kotenko et al., "Human cytomegalovirus harbors its own unique IL–10 homolog (cmvIL–10)." Proc. Natl. Acad. Sci. USA 97(4):1695–1700 (Feb. 15, 2000).
Kotenko et al. "Identification of the Functional Interleukin–22 (IL–22) Receptor Complex." J. Biol. Chem. 276(4):2725–2732 (Jan. 26, 2001).
Liang and Pardee, "Differential display of eukaryotic messenger RNA by means of the polymerase chain reaction." Science 257:967–971 (1992).
Liang et al., "Ras activation of novel genes: Mob–1 as a model." Proc. Natl. Acad. Sci USA 91:12515–12519 (Dec. 1994).
Liang et al., "Differential display using one–base anchored oligo–dT primer." Nucl. Acids Res. 22:5763–5764 (1994).
Liang, "Factors ensuring successful use of differential display." Methods 16:361–364 (1998).
Liu et al., "Expression Cloning and Characterizationof a Human IL–10 Receptor." J. Immunol 152;1821–1829 (1994).
McCarthy et al., "Rapid induction of heparin–binding epidermal growth factor/diphtheria toxin receptor expression by Raf and Ras oncogenes." Genes Dev. 9:1953–1964 (1995).
Moore et al., "Homology of cytokine synthesis inhibitory factor (IL–10) to Epstein–Barr virus gene BCRFI." Science 248:1230–1234 (1990).
Schaefer et al. "Cutting Edge: FISP (IL–4–Induced Secreted Protein), a Novel Cytokine–Like Molecule Secreted by Th2 Cells." J. Cell immunol 166:5859–5863 (2001).
Soo et al., "Cutaneous rat wounds express C49a, a novel gene with homology to human differentiation associated gene, Mda–7." J. Cell. Biochem. 74:1–10 (1999).
Tan et al., "Characterization of Recombinant Extracellular Domain of Human Interleukin–10 Receptor." J. Biol. Chem. 270:12906–12911 (May 26, 1995).

(Continued)

Primary Examiner—Lorraine Spector
Assistant Examiner—Stephen Gucker
(74) Attorney, Agent, or Firm—Needle & Rosenberg, P.C.

(57) ABSTRACT

The present invention provides the receptors for Mob-5 (IL-24). One of the Mob-5 receptors comprises IL-22R1 and IL-20R2. Another Mob-5 receptor comprises IL-20R1 and IL-22R2. The invention also provides methods of inhibiting the Mob-5 receptor as well as methods of detecting cancer by detecting the presence of the Mob-5 receptor.

4 Claims, 7 Drawing Sheets

OTHER PUBLICATIONS

Wang et al., "IL–10 Inhibit Transcription of Cytokine Genes in Human Peripheral Blood Mononuclear Cells." *J. Immunol.* 153:811–816 (1994).

Xie et al., "Interleukin (IL)–22, a Novel Human Cyotkine That Signals through the Interferon Receptor–related proteins CRF2–4 and IL–22R." *J. Biol. Chem.* 275(40):31335–31339 (Oct. 6, 2000).

Zhang et al., "Identification of a Novel Ligand–Receptor Pair Constitutively Activated by *ras* Oncogenes." 275(32):24436–24443 (Aug. 11, 2000).

Zhang et al., "Identification of rCop–1, a New Member of Ccn Gene Family, as a Negative Regulator for Cell Transformation." *Mol. Cell. Biol.* 18:6131–6141 (1998).

* cited by examiner

HUMAN MOB-5 (IL-24) RECEPTORS AND USES THEREOF

This application claims priority to provisional U.S. Patent Application No. 60/315,684, filed Aug. 29, 2001, which is incorporated herein by reference in its entirety.

This invention was made with government support under Grant CA74067 from the National Institutes of Health. The U.S. Government may have certain rights in this invention.

BACKGROUND OF THE INVENTION

1. Field of the Invention

This invention relates to the receptors for human Mob-5 (IL-24), and the detection of Mob-5 receptor expression and/or the presence of the Mob-5 receptor as potential markers for the early diagnosis of cancer. Methods for inhibiting the interaction between Mob-5 and the Mob-5 receptors are also provided.

2. Background Art

Mob-5 (IL-24), a gene constitutively activated by oncogenic Ras, encodes a secreted protein that exhibits significant homology to the IL-10 family of cytokines (See U.S. application Ser. No. 60/178,185, which is herein incorporated by reference in its entirety). To provide insight into the biochemical and biological functions of Mob-5/Mda-7 in normal development as well as during cell transformation and tumorigenesis, the present invention provides the identification and characterization of its functional cell surface receptor. This invention shows that Mob-5 is normally expressed in activated PBMCs (peripherial blood mononuclear cells) and its expression is deregulated in cancer tissues. Namely, under normal circumstances, Mob-5 (IL-24) is secreted by T cells and binds to its receptors on target cells at the site of infection or injury to promote healing, which involves proliferation. This invention shows that, in cancer, activation of oncogenes such as ras and the loss of p53 tumor-suppressor genes lead to over expression of both Mob-5 and its receptors in the same cells. Thus, such autocrine loops allow cancer cells to stimulate themselves for unregulated cell proliferation. The present invention provides compositions and methods for inhibiting or blocking these autocrine loops, thus inhibiting cancer. Furthermore, the present invention provides the surprising discovery that Mob-5 binds to a Mob-5 receptor that consists of a new combination of two previously known class II cytokine receptor subunits, thus providing a strong molecular basis for cross-talk among the IL-10 family of cytokines.

SUMMARY OF THE INVENTION

Figure 1:
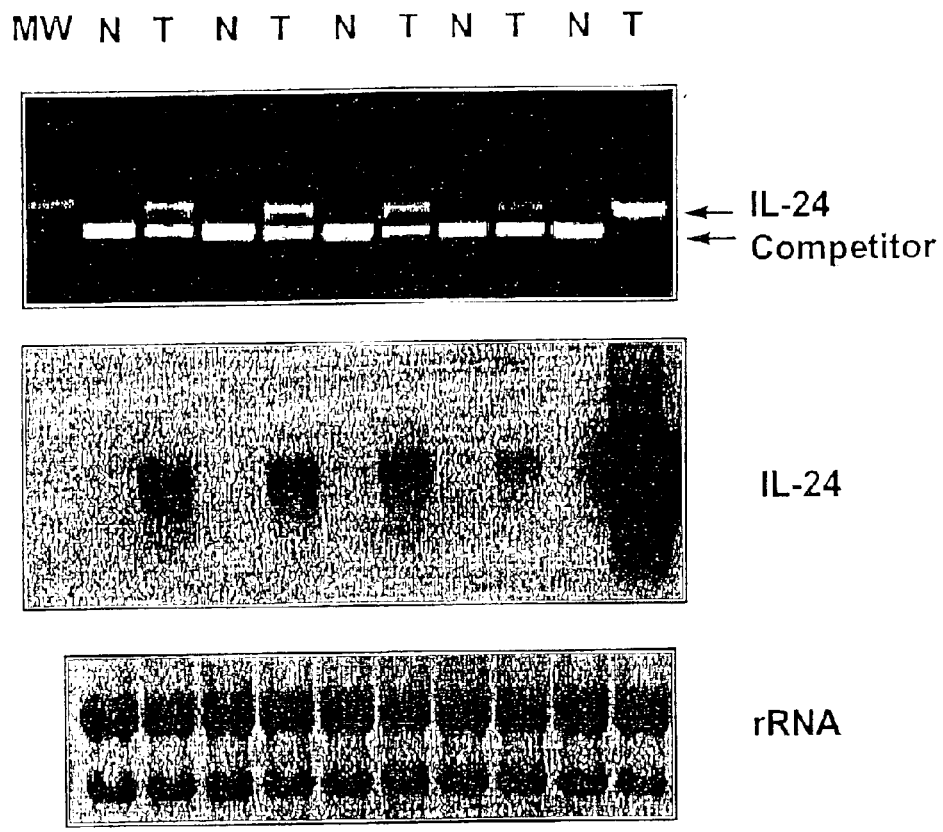
FIG. 1A shows the differential expression of the IL-24 mRNA in human colorectal cancer. Total RNA from pairwise matched cancer tissues and their adjacent normal tissues from five patients were analyzed by either quantitative RT-PCR (top panel) or regular RT-PCR followed by Southern blot using a IL-24 cDNA probe (middle panel). The image from rRNAs used for the analysis was shown as a control for equal sample loading.
FIG. 1B shows the induction of IL-24 by activated PBMCs. Freshly prepared human PBMCs were treated with PBS, LPS or ConA for 2 and 4 hours. The resulting conditioned media were subsequently analyzed by western blot analysis which showed that ConA, but not LPS, was able to cause a rapid induction of IL-24.
Figure 1:
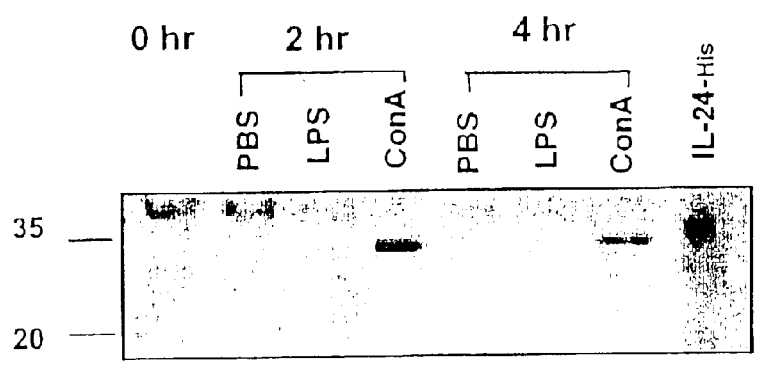

The present invention provides a composition comprising a complex between IL-22R1 and IL-20R2, a composition comprising a complex between Mob-5 (IL-24) and IL-22R1 and IL-20R2, a composition comprising a complex between Mob-5 (IL-24) and IL-20R1 and IL-20R2, a composition comprising a complex between Mob-5 (IL-24) and IL-22R1, a composition comprising a complex between Mob-5 (IL-24) and IL-20R2 and a composition comprising a complex between Mob-5 (IL-24) and IL-20R1.

The invention further provides purified antibodies that bind to the complexes of the present invention.

Further provided by the present invention is a vector comprising a nucleic acid encoding IL-22R1 and IL-20R2, and a vector comprising a nucleic acid encoding IL-20R1 and IL-20R2.

A method for inhibiting cancer comprising inhibiting the Mob-5 receptor in a cell so as to inhibit Mob-5 induced cancer.

The invention also provides a method of inhibiting a cellular transformation phenotype induced by an oncogene whose product functions upstream of a mob-5 gene product, comprising inhibiting formation of a Mob-5 receptor in a cell containing the upstream oncogene so as to inhibit the expression of the cellular transformation phenotype of the upstream oncogene.

Also provided is a method for inhibiting a mob-5 induced cellular transformation phenotype comprising inhibiting the Mob-5 receptor in a cell so as to inhibit the expression of the mob-5 induced cellular transformation phenotype.

The invention also provides a method of detecting the presence of cancer in a patient comprising: contacting a sample from the patient with an antibody to a Mob-5 receptor; detecting the binding of the antibody with an antigen in the sample, wherein binding of antigen to the antibody indicates the presence of Mob-5 receptor antigen in the sample and wherein Mob-5 receptor antigen in the sample indicates the presence of cancer in the patient, thereby detecting the presence of cancer in the patient.

Further provided is a method of detecting the presence of cancer in a patient comprising: contacting a sample from the patient with a Mob-5 receptor antigen; detecting the binding of the antigen with an antibody in the sample, wherein binding of antigen to the antibody indicates the presence of Mob-5 receptor antibody in the sample and wherein Mob-5 receptor antibody in the sample indicates the presence of cancer in the patient, thereby detecting the presence of cancer in the patient.

The present invention also provides method of detecting the Mob-5 receptor comprising, contacting a cell with a labeled Mob-5, detecting the binding of the labeled Mob-5 to the cell, wherein binding of the labeled Mob-5 to the cell indicates the cell is a Mob-5 receptor expressing cell, thus detecting the Mob-5 receptor.

Also provided is a method of screening for an inhibitor of Mob-5 binding to the Mob-5 receptor comprising: a) contacting a Mob-5 receptor containing cell with a labeled Mob-5 protein and a putative inhibitor; and b) measuring the amount of labeled Mob-5 protein bound to the cells, such that a decrease in labeled Mob-5 protein binding as compared to Mob-5 protein binding in cells that were not contacted with the inhibitor, indicates the presence of an inhibitor of the interaction between Mob-5 and the Mob-5 receptor.

The present invention further provides a method of screening for an inhibitor of IL-22R1/IL-20R2 dimerization comprising: a) transfecting a cell with a plasmid containing a nucleic acid comprising a nucleic acid sequence encoding Il-22R1 and a plasmid comprising a nucleic acid sequence encoding Il-20R2; b) contacting the cell with a putative inhibitor and; c) measuring dimerization, wherein a decrease in dimerization in the cell of step b) as compared to dimerization in a cell that was not contacted with the putative inhibitor indicates the presence of an inhibitor of IL-22R1/IL-20R2 dimerization.

The invention also provides a method of screening for an inhibitor of IL-20R1/IL-20R2 dimerization comprising: a) transfecting a cell with a plasmid containing a nucleic acid comprising a nucleic acid sequence encoding Il-20R1 and a plasmid comprising a nucleic acid sequence encoding Il-20R2; b) contacting the cell with a putative inhibitor and; c) measuring dimerization, wherein a decrease in dimerization in the cell of step b) as compared to dimerization in a cell that was not contacted with the putative inhibitor indicates the presence of an inhibitor of IL-20R1/IL-20R2 dimerization.

Further provided is a method of detecting Mob-5 activation of a Mob-5 receptor comprising: a) contacting a cell with Mob-5; b) measuring STAT activation, wherein an increase in STAT activation in the cell of step a) as compared to STAT activation in a cell not contacted with Mob-5 indicates Mob-5 activation of a Mob-5 receptor.

Also provided is a method of screening for an inhibitor of Mob-5 activation comprising: a) contacting a Mob-5 receptor containing cell with Mob-5 and a putative inhibitor; b) measuring STAT activation, wherein a decrease in STAT activation in the cell of step a) as compared to a Mob-5 receptor containing cell that was not contacted with the putative inhibitor indicates the presence of an inhibitor of Mob-5 activation.

The present invention also provides a method of screening agents for anti-cancer activity comprising; a) administering the agent to a cancer cell; b) monitoring the activity of a Mob-5 receptor in the cell, whereby an inhibition of the activity of the Mob-5 receptor indicates the agent has anti-cancer activity, thereby screening the agent for anti-cancer activity.

DETAILED DESCRIPTION OF THE INVENTION

The present invention may be understood more readily by reference to the following detailed description of the preferred embodiments of the invention and the Examples included therein.

Before the present compounds and methods are disclosed and described, it is to be understood that this invention is not limited to specific proteins, specific methods, or specific nucleic acids, as such may, of course, vary. It is also to be understood that the terminology used herein is for the purpose of describing particular embodiments only and is not intended to be limiting.

It must be noted that, as used in the specification and the appended claims, the singular forms "a," "an," and "the" include plural referents unless the context clearly dictates otherwise. Thus, for example, reference to "a nucleic acid" includes multiple copies of the nucleic acid and can also include more than one particular species of nucleic acid molecule.

Mob-5 (Il-24) Receptors

The present invention provides receptors for human Mob-5 or IL-24. One receptor is comprised of IL-22R1 and IL-20R2 and another receptor is comprised of IL-20R1 and IL-20R2. The present invention also contemplates receptor subunits, for example, IL-22R1, IL-20R2 and IL-20R1 as well as fragments of the receptor and fragments of the receptor subunits.

The nucleic acid sequence encoding IL-22R1 (SEQ ID NO: 4) and the amino acid sequence of IL-22R1 (SEQ ID NO: 5) can be accessed on GenBank via Accession No. NM_021258. IL-22R1 has also been described in the literature. (See Kotenko et al. "Identification of the functional interleukin-22 (IL-22) receptor complex: the IL-10R2 chain (IL-10Rbeta) is a common chain of both the IL-10 and IL-22 (IL-10-related T cell-derived inducible factor, IL-TIF) receptor complexes," *J. Biol. Chem.* 276(4), 2725–2732 (2001) and Xie et al. "Interleukin (IL)-22, a Novel Human Cytokine That Signals through the Interferon Receptor-related Proteins CRF2–4 and IL-22R," *J. Biol. Chem.* 275 (40), 31335–31339 (2000)) which references are herein incorporated by reference in their entireties.

The nucleic acid sequence encoding IL-20R1 (SEQ ID NO: 6) and the amino acid sequence of IL-20R1 (SEQ ID NO: 7) can be accessed on GenBank via Accession No. AF184971. IL-20R1 has also been described in the literature. (See U.S. Pat. No. 5,945,511 and Blumberg et al. "Interleukin 20: discovery, receptor identification, and role in epidermal function," *Cell.* 104(1):9–19 (2001)) which references are herein incorporated by reference in their entireties.

The nucleic acid sequence encoding IL-20R2 and the amino acid sequence of IL-20R2 has been described and published in International Patent Publication WO 99/46379 which reference is herein incorporated by reference in its entirety.

It is understood that, where desired, modification and changes may be made to the receptors, receptor subunits and receptor subunit fragments described herein and still obtain a protein having like or otherwise desirable characteristics. These modifications include insertions, deletions and point mutations. Such changes may occur in natural isolates or may be synthetically introduced using site-specific mutagenesis, the procedures for which, such as mis-match polymerase chain reaction (PCR), are well known in the art.

For example, certain amino acids may be substituted for other amino acids in a receptor without appreciable loss of functional activity of the Mob-5 receptor. These substitutions can occur in either subunit comprising the receptor or in both subunits. Since it is the interactive capacity and nature of a protein that defines that protein's biological functional activity, certain amino acid sequence substitutions can be made in a Mob-5 receptor amino acid sequence (or, of course, the underlying nucleic acid sequence) and nevertheless obtain a Mob-5 receptor protein with like properties. It is thus contemplated that various changes may be made in the sequence of the Mob-5 receptor amino acid sequence (or underlying nucleic acid sequence) without appreciable loss of biological utility or activity and possibly with an increase in such utility or activity.

It is also understood that the Mob-5 receptors of this invention may also contain conservative substitutions where a naturally occurring amino acid is replaced by one having similar properties and which does not alter the function of the polypeptide. Such conservative substitutions are well known in the art. Thus, it is understood that, where desired, modifications and changes may be made in the nucleic acid and/or amino acid sequence of the Mob-5 receptor protein of the present invention and still obtain a Mob-5 receptor protein having like or otherwise desirable characteristics.

The Mob-5 receptor polypeptides of this invention can be obtained via recombinant methods where a vector containing a nucleic acid encoding the polypeptide of interest can be introduced into an expression system that is capable of producing the polypeptide. These polypeptides can also be obtained in any of a number of procedures well known in the art. One method of producing a polypeptide is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a particular protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a larger polypeptide. (Grant, A Synthetic Peptides: A User Guide, "W.H. Freeman and Co., N.Y. (1992) and Bodansky and Trost, Ed., A Principles of Peptide Synthesis," Springer-Verlag Inc., N.Y. (1993)). Alternatively, the peptide or polypeptide can be independently synthesized in vivo as described above. Once isolated, these independent peptides or polypeptides may be linked to form a larger protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al. Biochemistry, 30:4151 (1991)). Alternatively, native chemical ligation of synthetic peptides can be utilized to synthetically construct large peptides or polypeptides from shorter peptide fragments. This method consists of a two-step chemical reaction (Dawson et al. "Synthesis of Proteins by Native Chemical Ligation," *Science*, 266:776–779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis et al. FEBS Lett., 307:97 (1987), Clark-Lewis et al., J.Biol.Chem., 269:16075 (1994), Clark-Lewis et al. Biochemistry, 30:3128 (1991), and Rajarathnam et al. Biochemistry, 29:1689 (1994)).

Alternatively, unprotected peptide segments can be chemically linked where the bond formed between the peptide segments as a result of the chemical ligation is an unnatural (non-peptide) bond (Schnolzer et al. Science, 256:221 (1992)). This technique has been used to synthesize analogs of protein domains as well as large amounts of relatively pure proteins with full biological activity (deLisle Milton et al. "Techniques in Protein Chemistry IV, Academic Press, New York, pp. 257–267 (1992)).

The present invention also provides a composition comprising a complex between IL-22R1 and IL-20R2. Therefore, compositions of the present invention include complexes formed by the interaction of IL-22R1 with IL-20R2. Further provided is a composition comprising a complex between IL-20R1 and IL-20R2. Therefore, compositions of the present invention include complexes formed by the interaction of IL-20R1 with IL-20R2. Also provided by this invention is a composition comprising a complex between Mob-5 (IL-24) and IL-22R1 and IL-20R2 as well as a composition comprising a complex between Mob-5 (IL-24) and IL-20R1 and IL-20R2. Further provided is a composition comprising a complex between Mob-5 (IL-24) and IL-22R1. Also provided is a composition comprising a complex between Mob-5 (IL-24) and IL-20R2. The invention also provides a composition comprising a complex between Mob-5(IL-24) and IL-20R1.

The present invention also provides a composition comprising a soluble form of the Mob-5 receptor formed by the extracellular portions of IL-22R1 and IL-20R2 or the extracellular portions of IL-20R1 and IL-20R2. For example, the present invention provides amino acids 1–226 of IL-22R1 (SEQ ID NO: 1) as a soluble extracellular portion of IL-22R1 that can be combined with amino acids 1–229 of IL-20R2 (SEQ ID NO: 2) to form a soluble Mob-5 receptor. This invention further provides amino acids 1–248 of IL-20R1 (SEQ ID NO: 3) that can be combined with amino acids 1–229 of IL-20R2 (SEQ ID NO: 2) to form a soluble Mob-5 receptor. Fragments of SEQ ID NO: 1, SEQ ID NO: 2 and SEQ ID NO: 3 are also provided which can be combined to form a soluble Mob-5 receptor. The present invention also provides the use of the individual receptor subunits, i.e. SEQ ID NO: 1, SEQ ID NO:2 or SEQ ID NO: 3 and fragments thereof as soluble receptors for Mob-5. One of skill in the art would know how to construct soluble Mob-5 receptors and test these soluble Mob-5 receptors for Mob-5 binding as described herein and as known in the art in order to obtain soluble forms of the Mob-5 receptor that retain Mob-5 binding ability. These soluble forms of the Mob-5 receptor can be utilized to block Mob-5 binding to Mob-5 receptors by competing with Mob-5 receptors for the binding of Mob-5.

Mob-5 Receptor Nucleic Acids

The present invention provides an isolated nucleic acid encoding the receptors, receptor subunits and peptides of the invention. For example, the invention provides an isolated nucleic acid encoding IL-22R1 and IL-20R2. The present invention also provides an isolated nucleic acid encoding IL-20R1 and IL-20R2. Furthermore, the present invention provides nucleic acids encoding IL-22R1, IL-20R1 or IL-20R2 and fragments thereof.

A nucleic acid of this invention encodes both proteins (IL-22R1 and IL-20R2) that comprise a heterodimeric receptor for Mob-5 (IL-24). Another nucleic acid of this invention encodes both proteins (IL-20R1 and IL-20R2) that comprise another heterodimeric receptor for Mob-5 (IL-24). As used herein, the term "nucleic acid" refers to single-or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the genes discussed herein or may include alternative codons which encode the same amino acid as that which is found in the naturally occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

The nucleic acids provided for by the present invention may be obtained in any number of ways. For example, DNA molecules encoding IL-22R1, IL-22R1 or IL-20R2 can be obtained from commercial sources as well as from academic laboratories. Also, a DNA molecule encoding IL-22R1 or IL-20R2 protein can be isolated from the organism in which it is normally found. For example, a genomic DNA or cDNA library can be constructed and screened for the presence of the gene or nucleic acid of interest. Methods of constructing and screening such libraries are well known in the art and kits for performing the construction and screening steps are commercially available (for example, Stratagene Cloning Systems, La Jolla, Calif.). Once isolated, the gene or nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Once the gene or nucleic acid sequence of the desired protein is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type protein coding sequence in order to obtain any of a number of possible combinations of amino acids at any position of the protein. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423–462 (1985) and Zoller, M. J. "New molecular biology methods for protein engineering" Curr. Opin. Struct. Biol., 1:605–610 (1991). Techniques such as these can also be used to modify the genes or nucleic acids in regions other than the coding regions, such as the promoter regions for IL-22R1 and IL-20R2. Likewise, these techniques can be used to alter the coding sequence without altering the amino acid sequence that is encoded.

Another example of a method of obtaining a DNA molecule encoding a specific Mob-5 receptor protein is to synthesize a recombinant DNA molecule which encodes the Mob-5 receptor proteins. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330–1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599–603 (1986), wherein synthesis of a 1057 base pair synthetic bovine rhodopsin gene from synthetic oligonucleotides is disclosed. By constructing a Mob-5 receptor protein, i.e. IL-22R1 and/or IL-20R2, in this manner, one skilled in the art can readily obtain any particular Mob-5 receptor protein with desired amino acids at any particular position or positions within the Mob-5 receptor protein. See also, U.S. Pat. No. 5,503,995 which describes an enzyme template reaction method of making synthetic genes. Techniques such as this are routine in the art and are well documented. These nucleic acids or fragments of a nucleic acid encoding Mob-5 receptor proteins can then be expressed in vivo or in vitro as discussed below.

The invention also provides for the isolated nucleic acids encoding IL-22R1 and IL-20R2 in a vector suitable for expressing the nucleic acid. The invention also contemplates a vector comprising an isolated nucleic acid encoding IL-22R1 and a vector comprising an isolated nucleic acid encoding IL-20R2 for contransfection of cells to obtain recombinant cells expressing both IL-22R1 and IL-20R2.

The invention also provides for the isolated nucleic acids encoding IL-20R1 and IL-20R2 in a vector suitable for expressing the nucleic acid. Also provided by this invention is a vector comprising an isolated nucleic acid encoding IL-20R1 and a vector comprising an isolated nucleic acid encoding IL-20R2 for contransfection of cells to obtain recombinant cells expressing both IL-20R1 and IL-20R2.

Once a nucleic acid encoding IL-22R1 and IL-20R2, or a nucleic acid encoding IL-20R1 and IL-20R2, or a region of that nucleic acid, is constructed, modified, or isolated, that nucleic acid can then be cloned into an appropriate vector, which can direct the in vivo or in vitro synthesis of that wild-type and/or modified Mob-5 receptor proteins. The vector is contemplated to have the necessary functional elements that direct and regulate transcription of the inserted gene, or nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., "α-Factor-Directed Synthesis and Secretion of Mature Foreign Proteins in *Saccharomyces cerevisiae*." Proc. Nat. Acad. Sci., 81:4642–4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexin 1, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice.

The invention also provides for the vectors containing the contemplated nucleic acids in a host suitable for expressing the nucleic acids. The vectors containing the nucleic acid segments of interest can be transferred into host cells by well-known methods, which vary depending on the type of cellular host. For example, calcium chloride transformation, transduction, and electroporation are commonly utilized for prokaryotic cells, whereas calcium phosphate, DEAE dextran, or lipofection mediated transfection or electroporation may be used for other cellular hosts.

Alternatively, the genes or nucleic acids of the present invention can be operatively linked to one or more of the functional elements that direct and regulate transcription of the inserted gene as discussed above and the gene or nucleic acid can be expressed. For example, a gene or nucleic acid can be operatively linked to a bacterial or phage promoter and used to direct the transcription of the gene or nucleic acid in vitro. A further example includes using a gene or nucleic acid provided herein in a coupled transcription-translation system where the gene directs transcription and the RNA thereby produced is used as a template for translation to produce a polypeptide. One skilled in the art will appreciate that the products of these reactions can be used in many applications such as using labeled RNAs as probes and using polypeptides to generate antibodies or in a procedure where the polypeptides are being administered to a cell or a patient.

Expression of the gene or nucleic acid, in combination with a vector, can be by either in vivo or in vitro. In vivo synthesis comprises transforming prokaryotic or eukaryotic cells that can serve as host cells for the vector. Alternatively, expression of the gene or nucleic acid can occur in an in vitro expression system. For example, in vitro transcription systems are commercially available which are routinely used to synthesize relatively large amounts of mRNA. In such in vitro transcription systems, the nucleic acid encoding the Mob-5 receptor proteins would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired Mob-5 receptor protein. (Stratagene Cloning Systems, La Jolla, Calif.). High quantity expression and production of the Mob-5 receptor protein can also be achieved by transgenic animal technology by which animals can be made to produce Mob-5 receptor protein, or soluble Mob-5 receptor in serum, milk, etc in large amounts.

Mob-5 Receptor Antibodies

Also provided herein are purified antibodies that selectively or specifically bind to the complexes provided and contemplated herein. Antibodies that specifically bind to the complexes do not bind to individual components of the complex. For example, purified antibodies which selectively or specifically bind to a complex between IL-22R1 and IL-20R2 do not bind to IL-22R1 in the absence of Il-20R2 nor does it bind to IL-20R2 in the absence of Il-22R1. Therefore, an antibody that binds to the complex formed between IL-22R1 and IL-20R2 is specific for the Mob-5 receptor that is formed by the dimerization of these two proteins.

Antibodies that bind to a complex between Mob-5 (IL-24) and IL-22R1 and IL-20R2 are also provided. Also provided are antibodies that bind to a complex between Mob-5 (IL-24) and IL-20R1 and IL-20R2. Further provided is an antibody that binds to a complex between Mob-5 (IL-24) and IL-22R1. Also provided is an antibody that binds to a complex between Mob-5 (IL-24) and IL-20R2. The invention also provides an antibody that binds to a complex between Mob-5 (IL-24) and IL-20R1. Antibodies that bind to Mob-5, IL-20R1, IL-22R1 or IL-20R2 or fragments thereof are also contemplated herein.

Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al. *Bio/Technology*, 10:163–167 (1992); Bebbington et al. *Biotechnology*, 10:169–175 (1992)). Humanized and chimeric antibodies are also contemplated in this invention. Heterologous antibodies can be made by well known methods (See, for example, U.S. Pat. Nos. 5,545,806, 5,569,825, 5,625,126, 5,633,425, 5,661,016, 5,770,429, 5,789,650, and 5,814,318).

The phrase "specifically binds" with the polypeptide refers to a binding reaction which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

The term "antibody" is used herein in a broad sense and includes intact immunoglobulin molecules and fragments or polymers of those immunoglobulin molecules, so long as they exhibit any of the desired properties described herein. Antibodies are typically proteins which exhibit binding specificity to a specific antigen. Native antibodies are usually heterotetrameric glycoproteins, composed of two light (L) chains and two heavy (H) chains. The heavy and light chains are typically identical, but not necessarily so. Typically, each light chain is linked to a heavy chain by one or more covalent disulfide bond, while the number of disulfide linkages varies between the heavy chains of different immunoglobulin isotypes. Each heavy and light chain also typically has regularly spaced intrachain disulfide bridges. Each heavy chain typically has at one end a variable domain (V(H)) followed by a number of constant domains. Each light chain typically has a variable domain at one end (V(L)) and a constant domain at its other end; the constant domain of the light chain is typically aligned with the first constant domain of the heavy chain, and the light chain variable domain is typically aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can typically be assigned to different classes. There are approximately five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, δ, ε, γ, and μ, respectively.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β.-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest" National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain may be identical with or homologous to corresponding sequences in antibodies derived from a particular species or belonging to a particular antibody class or subclass, while the remainder of the chain(s) may be identical with or homologous to corresponding sequences in antibodies derived from another species or belonging to another antibody class or subclass, as well as fragments of such antibodies, so long as they exhibit the desired antagonistic activity (See, U.S. Pat. No. 4,816,567 and Morrison et al., Proc. Natl. Acad. Sci. USA, 81:6851–6855 (1984)).

The antibody (either polyclonal or monoclonal) can be raised to any of the polypeptides provided and contemplated herein, both naturally occurring and recombinant polypeptides, and immunogenic fragments, thereof. The antibody can be used in techniques or procedures such as diagnostics, treatment, or vaccination. Anti-idiotypic antibodies and affinity matured antibodies are also considered.

The antibodies of the invention include anti-Mob 5 receptor antibodies and anti-Mob 5 antibodies that may further comprise humanized antibodies or human antibodies. Humanized forms of non-human (e.g., murine) antibodies are chimeric immunoglobulins, immunoglobulin chains or fragments thereof (such as Fv, Fab, Fab' or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986), Reichmann et al., Nature, 332:323–327 (1988), and Presta, Curr. Op. Struct. Biol., 2:593–596 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522–525 (1986), Riechmann et al., Nature, 332:323–327 (1988), Verhoeyen et al., Science, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody (Sims et al., J. Immunol., 151:2296 (1993) and Chothia et al, J. Mol. Biol., 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding (see, WO 94/04679 published 3 Mar. 1994).

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551–255 (1993); Jakobovits et al., Nature, 362:255–258 (1993); Bruggennann et al., Year in Immuno., 7:33 (1993)). Human antibodies can also be produced in phage display libraries [Hoogenboom et al., J. Mol. Biol., 227:381 (1991); Marks et al., J. Mol. Biol., 222:581 (1991)]. The techniques of Cote et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)].

The purified antibodies of this invention include monoclonal antibodies which can be used for diagnostic or analytical purposes. For example, the monoclonal antibody could be utilized in a clinical testing kit to monitor levels of Mob-5 receptor in human tissues or secretions.

Detection Methods

The present invention also provides a method of detecting the Mob-5 receptor comprising, contacting a cell with a labeled Mob-5, detecting the binding of the labeled Mob-5 to the cell, wherein binding of the labeled Mob-5 to the cell indicates the cell is a Mob-5 receptor expressing cell, thus detecting the Mob-5 receptor.

In the methods of the present invention, the labeled Mob-5 includes $^{125}$I-labeled Mob-5, a Mob-5-alkaline phosphatase fusion protein (Mob-5-AP), a Mob-5-IGg Fc fusion protein, a horse radish peroxidase (HRP) labeled Mob-5, a biotin labeled Mob-5 and any other Mob-5 linked to a detectable moiety. One of skill in the art would know how to measure the amounts of labeled Mob-5 in the methods of the present invention based on the teachings set forth in the Examples and those well known in the art.

The present invention further provides a method of detecting Mob-5 activation of a Mob-5 receptor comprising: a) contacting a cell with Mob-5; b) measuring STAT activation, wherein an increase in STAT activation in the cell of step a) as compared to STAT activation in a cell not contacted with Mob-5 indicates Mob-5 activation of a Mob-5 receptor. One of skill in the art would know how to measure STAT activation based on the teachings set forth in the Examples as well as teachings known in the art.

In the methods of the present invention, the Mob-5 receptor can be the IL-20R1/IL-20R2 heterodimer or the IL-22R1/IL-20R2 heterodimer or both.

Methods of Inhibiting Mob-5 Receptors

Also provided by the present invention is a method for inhibiting a mob-5 induced cellular transformation phenotype comprising inhibiting the Mob-5 receptor in a cell so as to inhibit the expression of the mob-5 induced cellular transformation phenotype.

Further provided by the present invention is a method for inhibiting a Mob-5 induced cancer comprising inhibiting the Mob-5 receptor in a cell so as to inhibit the Mob-5 induced cancer.

In this invention, "cellular transformation phenotype" means that cells have undergone at least some transformation characterized by one or more morphologic or biochemical changes such as loss of contact inhibition, increased rate of glycolysis, alterations of the cell surface and other changes that would be known to one skilled in the art. Other changes include increased ability to grow in soft agar and increased tumorogenicity in nude mice.

In this invention, "inhibition of cancer" or "inhibition of cancer formation" means partial or total killing of cancerous cells, reduction in tumor size, disappearance of a tumor, inhibition of tumor growth, inhibition of vascularization, inhibition of cellular proliferation, an induction in dormancy or an apparent induction of dormancy, or a decreased metastasis of a tumor or a tumor cell. These mechanisms of action are only exemplary of the ways that an inhibitor of the Mob-5 receptor can inhibit or treat cancer. The methods of the present invention can be utilized to inhibit or treat various types of cancers including, but not limited to, pancreatic cancer, skin cancer, larynx cancer, lung cancer, breast cancer, adrenocarcinoma and colon cancer.

The term "inhibiting" is familiar to one skilled in the art and is used herein to describe any compound or composition which inhibits or decreases the expression or activity of a Mob-5 receptor. The degree of inhibition does not have to be complete, such as completely inhibiting the expression or activity of a Mob-5 receptor and therefore comprises any inhibition of the expression or activity of the Mob-5 receptor relative to the expression of the Mob-5 receptor in a similar environment in the absence of the inhibiting compound. Inhibition can occur in many ways such by inhibiting gene expression, inhibiting Mob-5 binding to Mob-5 receptor, inhibiting Mob-5 receptor activation, administering an antibody to a Mob-5 receptor, administering an antibody to a Mob-5 receptor subunit and by other methods known in the art.

The cellular transformation phenotype and/or cancer of this invention can be inhibited by disrupting dimerization between IL-22R1 and IL-20R2 in order to prevent a Mob-5 receptor from forming, thus preventing binding of Mob-5 to its receptor and effecting inhibition of a cellular transformation phenotype. For example, an anti-IL-22R1 antibody or an anti-IL-20R2 antibody can be utilized to disrupt dimerization. Fragments of IL-22R1 and IL-20R2 can also be utilized to disrupt dimerization. One of skill in the art could identify the contact points between the subunits and design peptides that would disrupt dimerization. For example, crystal structures of IL-22R1 and Il-20R2 and their complexes may be utilized to design molecules that disrupt Mob-5 binding to its receptor.

The cellular transformation phenotype and/or cancer of this invention can also be inhibited by disrupting dimerization between IL-20R1 and IL-20R2 in order to prevent a Mob-5 receptor from forming, thus preventing binding of Mob-5 to its receptor and effecting inhibition of a cellular transformation phenotype. For example, an anti-IL-20R1 antibody or an anti-IL-20R2 antibody can be utilized to disrupt dimerization. Fragments of IL-20R1 and IL-20R2 can also be utilized to disrupt dimerization. One of skill in the art could identify the contact points between the subunits and design peptides that would disrupt dimerization. For example, crystal structures of IL-20R1 and Il-20R2 and their complexes may be utilized to design molecules that disrupt Mob-5 binding to its receptor.

Alternatively, an inhibitor of the Mob-5 receptor can be administered to a cell. An "inhibitor" is defined as a compound that binds a Mob-5 receptor including antibodies, that prevents an activity of a Mob-5 receptor. Upon binding to the receptor, the inhibitor can disrupt or prevent Mob-5 binding to the Mob-5 receptor. The inhibitor can be an antibody, either polyclonal or monoclonal, that specifically binds to a Mob-5 receptor, a ligand that binds to a Mob-5 receptor, a polypeptide that binds to a Mob-5 receptor or a compound that binds to a Mob-5 receptor. The inhibitor can also be an antibody, either either polyclonal or monoclonal, that specifically binds to a Mob-5 (ligand for the Mob-5 receptor), a ligand that binds to a Mob-5, a polypeptide that binds to Mob-5 or a compound that binds to a Mob-5 and thus prevents the interaction of Mob-5 with the Mob-5 receptor. Anti-idiotypic antibodies, affinity matured antibodies and humanized antibodies of Mob-5 receptor and Mob-5 are also considered. Other inhibitors include, but are not limited to molecules or compounds designed to block the binding of Mob-5 to the Mob-5 receptor. The inhibitor can be a whole protein or a fragment of a protein that inhibits binding, thus preventing Mob-5 receptor activation. The inhibitors can also be soluble fragments of the Mob-5 receptor that bind to Mob-5 and blocks the binding of Mob-5 to cell surface Mob-5 receptors.

A Mob-5 receptor can also be inhibited by administering to the cell an altered Mob-5 protein which binds to the Mob-5 receptor, whereby binding of the altered Mob-5 to the receptor inhibits the binding of Mob-5 to the receptor, thereby inhibiting the expression of a mob-5 induced cellular transformation phenotype.

The cellular transformation phenotype and/or cancer of this invention can be inhibited by a nucleic acid antisense to the Mob-5 receptor. For example, a nucleic acid antisense to the nucleic acid encoding IL-22R1 and/or a nucleic acid antisense to the nucleic acid encoding IL-20R2 can be utilized to inhibit expression of the genes that comprise a Mob-5 receptor. A nucleic acid antisense to the nucleic acid encoding IL-20R1 and/or a nucleic acid antisense to the nucleic acid encoding IL-20R2 can also be utilized to inhibit expression of the genes that comprise a Mob-5 receptor. Antisense technology is well known in the art and describes a mechanism whereby a nucleic acid comprising a nucleotide sequence which is in a complementary, "antisense" orientation with respect to a coding or "sense" sequence of an endogenous gene, is introduced into a cell, whereby a duplex may form between the antisense sequence and its complementary sense sequence. The formation of this duplex may result in inactivation of the endogenous gene.

For example, the antisense nucleic acid can inhibit gene expression by forming an RNA/RNA duplex between the antisense RNA and the RNA transcribed from a target gene. The precise mechanism by which this duplex formation decreases the production of the protein encoded by the endogenous gene most likely involves binding of complementary regions of the normal sense mRNA and the antisense RNA strand with duplex formation in a manner that blocks RNA processing and translation. Alternative mechanisms include the formation of a triplex between the antisense RNA and duplex DNA or the formation of a DNA-RNA duplex with subsequent degradation of DNA-RNA hybrids by RNAse H. Furthermore, an antisense effect can result from certain DNA-based oligonucleotides via triple-helix formation between the oligomer and double-stranded DNA which results in the repression of gene transcription. Antisense nucleic acid can be produced for any relevant endogenous gene for which the coding sequence has been or can be determined according to well known methods.

A nucleic acid encoding an antisense RNA can be selected based on the protein desired to be inhibited or decreased in cells, by providing an RNA that will selectively bind to the cellular mRNA encoding such protein. Binding of the antisense molecule to the target mRNA may incapacitate the mRNAs, thus preventing its translation into a functional protein. The antisense RNA/mRNA complexes can then become a target for RNAse-H and are eventually degraded by the host cell RNAse-H. Control regions, such as enhancers and promoters, can be selected for antisense RNA targeting according to the cell or tissue in which it is to be expressed, as is known in the art. Preferable antisense-encoding constructs can encode full-length complements to target sequences; however, smaller length sequences down to oligonucleotide size can be utilized. For example, the antisense-encoding constructs can encode full-length complements to the mob-5 gene, smaller length sequences or oligonucleotide sequences.

The present invention further provides a method of inhibiting a cellular transformation phenotype and/or cancer induced by an oncogene whose product functions upstream of a mob-5 gene product, comprising inhibiting formation of a Mob-5 receptor in a cell containing the upstream oncogene so as to inhibit the expression of the cellular transformation phenotype of the upstream oncogene. For example, by inhibiting formation of a Mob-5 receptor in a cell, the cellular transformation phenotype of upstream oncogenes such as ras-oncogene, MAP kinase and raf can be inhibited.

The term "oncogene" refers to genes that produce products involved in altering cellular metabolism and often stimulate unregulated growth associated with malignant transformation of cells. Examples of oncogenes include but are not limited to, ras, src, myc, and fos. The cellular transformation phenotype of this invention can be induced by a ras oncogene product.

Screening Methods

The present invention also provides a method of screening for an inhibitor of IL-22R1/IL-20R2 dimerization comprising: a) transfecting a cell with a plasmid containing a nucleic acid comprising a nucleic acid sequence encoding Il-22R1 and a plasmid comprising a nucleic acid sequence encoding Il-20R2; b) contacting the cell with a putative inhibitor and; measuring dimerization, wherein a decrease in dimerization in the cell of step b) as compared to dimerization in a cell that was not contacted with the putative inhibitor indicates the presence of an inhibitor of IL-22R1/IL-20R2 dimerization.

The present invention also provides a method of screening for an inhibitor of IL-22R1/IL-20R2 dimerization comprising: a) contacting the cell comprising a nucleic acid sequence encoding IL-22R1 and a nucleic acid sequence encoding IL-20R2 with a putative inhibitor and; b) measuring dimerization, wherein a decrease in dimerization in the cell of step a) as compared to a cell comprising a nucleic acid sequence encoding IL-22R1 and a nucleic acid sequence encoding IL-20R2 that was not contacted with the putative inhibitor indicates the presence of an inhibitor of IL-22R1/IL-20R2 dimerization.

The present invention further provides a method of screening for an inhibitor of IL-20R1/IL-20R2 dimerization comprising: a) transfecting a cell with a plasmid containing a nucleic acid comprising a nucleic acid sequence encoding Il-20R1 and a plasmid comprising a nucleic acid sequence encoding Il-20R2; b) contacting the cell with a putative inhibitor and; measuring dimerization, wherein a decrease in dimerization in the cell of step b) as compared to dimerization in a cell that was not contacted with the putative inhibitor indicates the presence of an inhibitor of IL-20R1/IL-20R2 dimerization.

Also provided by the present invention is a method of screening for an inhibitor of IL-20R1/IL-20R2 dimerization comprising: a) contacting a cell comprising a nucleic acid sequence encoding IL-20R1 and a nucleic acid sequence encoding IL-20R2 with a putative inhibitor and; b) measuring dimerization, wherein a decrease in dimerization in the cell of step a) as compared to dimerization in a cell comprising a nucleic acid sequence encoding IL-20R1 and a nucleic acid sequence encoding IL-20R2 that was not contacted with the putative inhibitor indicates the presence of an inhibitor of IL-20R1/IL-20R2 dimerization.

An example of this screening method is a method of screening for an inhibitor of dimerization comprising: a) transfecting a cell with a plasmid containing a nucleic acid comprising a nucleic acid sequence encoding Il-20R1 functionally linked to a flourescence donor and a plasmid comprising a nucleic acid sequence encoding IL-20R2 functionally linked to a flourescence donor; b) contacting the cell with the inhibitor; and c) measuring fluorescence resonance energy transfer (FRET), wherein a decrease in FRET as compared to FRET measurement in a cell that was not contacted with the inhibitor indicates the presence of an inhibitor of Il-20R1/Il-20R2 dimerization.

In performing the screening methods described above, a single plasmid can be utilized to deliver both the nucleic acid encoding IL-22R1 and the nucleic acid encoding IL-20R2. Furthermore, either IL-22R1 or IL-20R2 can be linked to a donor or an acceptor. Similarly, a single plasmid can be utilized to deliver both the nucleic acid encoding IL-20R1 and the nucleic acid encoding IL-20R2. Furthermore, either IL-20R1 or IL-20R2 can be linked to a donor or an acceptor.

For dimerization measurements, one of skill in the art could measure the amount of dimerization in a cell comprising a nucleic acid sequence encoding IL-22R1 and a nucleic acid sequence encoding IL-20R2 before the addition of a putative inhibitor and then measure dimerization after the addition of the putative inhibitor. A decrease in dimerization after contacting the cell with the putative inhibitor is indicative of an inhibitor of IL-22R1/IL-20R2 dimerization. Alternatively, one of skill in the art could compare the amount of dimerization in cell comprising a nucleic acid sequence encoding IL-22R1 and a nucleic acid sequence encoding IL-20R2 after the addition of a putative inhibitor with the amount of dimerization in control cells comprising a nucleic acid sequence encoding IL-22R1 and a nucleic acid sequence encoding IL-20R2 that have not been contacted with the putative inhibitor. Similarly, the above dimerization measurements can be performed to determine the amount of dimerization between IL-20R1 and IL-20R2.

The present invention also contemplates a method of screening for an inhibitor of Mob-5 binding to the Mob-5 receptor comprising: contacting a Mob-5 receptor containing cell with a labeled Mob-5 protein and a putative inhibitor; measuring the amount of labeled Mob-5 protein bound to the cells, such that a decrease in labeled Mob-5 protein binding as compared to Mob-5 protein binding in cells that were not contacted with the inhibitor, indicates the presence of an inhibitor of the interaction between Mob-5 and the Mob-5 receptor. In the method described above, one of skill in the art would compare the amount of labeled Mob-5 bound to cells that have been contacted with a putative inhibitor with the amount of Mob-5 bound to cells that were not contacted with the inhibitor. A decrease in the amount of labeled Mob-5 bound to cells that have been contacted with a putative inhibitor as compared to labeled Mob-5 binding in cells that were not contacted with the inhibitor, indicates the presence of an inhibitor of the interaction between Mob-5 and the Mob-5 receptor.

The present invention also provides a method of screening for an inhibitor of Mob-activation comprising: a) contacting a Mob-5 receptor containing cell with Mob-5 and a putative inhibitor; and b) measuring STAT activation, wherein a decrease in STAT activation in the cell of step a) as compared to a Mob-5 receptor containing cell that was not contacted with the putative inhibitor indicates the presence of an inhibitor of Mob-5 activation.

The present invention also provides a method of screening agents for anti-cancer activity comprising; a) administering the agent to a cancer cell; b) monitoring the activity of a Mob-5 receptor in the cell, whereby an inhibition of the activity of the Mob-5 receptor indicates the agent has anti-cancer activity, thereby screening the agent for anti-cancer activity.

Cancer Detection

The present invention also provides a method of detecting the presence of cancer in a patient comprising: contacting a sample from the patient with an antibody to a Mob-5 receptor as described above; detecting the binding of the antibody with an antigen in the sample, wherein binding of antigen to the antibody indicates the presence of Mob-5 receptor antigen in the sample and wherein Mob-5 receptor antigen in the sample indicates the presence of cancer in the patient, thereby detecting the presence of cancer in the patient.

In this detection method, the amount of antibody that is bound to an antigen in the sample can be compared to the amount of antibody that is bound to antigen in a sample obtained from a patient that does not have cancer. If the amount of antibody that is bound to antigen in the sample from the patient suspected of having cancer is greater than the amount of antibody that is bound to antigen in the sample from the patient that does not have cancer, cancer is present in the patient suspected of having cancer. Alternatively, one of skill in the art would know how to compare the amount of antibody bound to antigen in the sample with the amount of Mob-5 receptor antigen detected in other cancer patients and thus, be able to determine whether or not the level of Mob-5 receptor detected corresponds to a cancerous condition.

The "subject" or "patient" of this method can be any animal. In a preferred embodiment, the animal of the present invention is a human. In addition, non-human animals which can be treated by the methods of this invention can include, but are not limited to, cats, dogs, birds, horses, cows, goats, sheep, guinea pigs, hamsters, gerbils and rabbits.

The sample of this invention can be from any organism and can be, but is not limited to, peripheral blood, plasma, urine, saliva, gastric secretion, feces, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. It is further contemplated that the biological sample of this invention can also be whole cells or cell organelles (e.g., nuclei). The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention.

The methods of the present invention can be utilized to detect various types of cancers including, but not limited to, pancreatic cancer, skin cancer, larynx cancer, lung cancer, breast cancer, adrenocarcinoma and colon cancer.

As used herein, "antigen" when used in the detection context generally means detecting the antigen, specifically the Mob-5 receptor, or a fragment thereof. The antigens of this invention can also be used to detect antibodies to the Mob-5 receptor or fragments thereof. In cancerous conditions, the antigen may exist on the cell surface as well as be detectable in a body fluid.

One example of the method of detecting the antigen is performed by contacting a fluid or tissue sample from the patient with an amount of a an antibody, possibly purified, reactive with the antigen, cells containing the antigen, or fragments of the antigen, and detecting the reaction of the antibody with the antigen. The fluid sample of this method can comprise any body fluid which would contain the antigen or a cell containing the antigen, such as blood, plasma, serum, saliva and urine, sputum, mucus and the like. An antibody used to detect the antigens of this invention is preferably specifically reactive with the antigen.

In the present invention, the step of detecting the binding of the antibody with the antigen can be further aided, in appropriate instances, by the use of a secondary antibody or other ligand which is reactive, either specifically with a different epitope or nonspecifically with the ligand or reacted antibody. The antibody can be labeled with a detectable marker.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. Other assays for detecting the binding of an antibody to an antigen can be used.

The present invention further provides a kit for detecting the binding of an antibody to the Mob-5 receptor, or a fragment thereof. Particularly, the kit can detect the presence of an antigen specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein. The particular reagents and other components included in the diagnostic kits of the present invention can be selected from those available in the art in accord with the specific diagnostic method practiced in the kit. Such kits can be used to detect the binding of the antibody with Mob-5 receptor, or a fragment thereof, in tissue and fluid samples from a patient.

One skilled in the art will be able to correlate the levels of Mob-5 receptor antigen detected using the methods disclosed herein with a particular stage of the cancer, thus utilizing the detection method for prognostic purposes. The prognostic evaluation can determine what type of anti-cancer therapy to employ at different stages of cancer depending on the amounts of Mob-5 receptor antigen detected in the patient's sample.

The invention also provides for a method of in vivo detection of Mob-5 receptor by administering an anti-Mob-5 receptor antibody conjugated to a tracer to a subject and imaging the anti-Mob-5 receptor antibody. Tracers that may be conjugated to the anti-Mob-5 receptor antibody are known in the art and include radiolabels such as 99mTc, 111In, 125I, 131I. Imaging techniques are also known in the art and include immunoscintography, single photon emission computed tomographic imaging and high-resolution gamma-camera imaging (Sato et al. 1999. "Intratumoral distribution of radiolabeled antibody and radioimmunotherapy in experimental liver metastases model of nude mouse" J. Nucl. Med. 40:685–692; Reilly 1993 "Immunoscintography of tumours using 99Tcm-labelled monoclonal antibodies: a review" Nucl. Med. Commun. 14:347–359.) One skilled in the art would be able to select the appropriate combination of tracer and imaging technique to detect the anti-Mob-5 receptor antibody in vivo. The in vivo imaging of anti-Mob-5 receptor antibody can be utilized for diagnostic purposes, prognostic purposes as well as for the intraoperative detection of metastatic deposits.

The invention also provides for a method of classifying a cancer as a colorectal cancer comprising, obtaining a sample from a patient diagnosed with cancer, contacting the sample with an antibody to Mob-5 receptor, and detecting the binding of the antibody with an antigen in the sample, wherein the binding of the antibody to the antigen indicated the cancer is colorectal cancer, thereby classifying the cancer as a colorectal cancer.

By "classifying" is meant to determine that the expression of Mob-5 corresponds to a specific type of cancer, such as colorectal cancer and not to another type of cancer, thus classifying the cancer. To ascertain that the cancer is, in fact, a colorectal cancer, the detection of Mob-5 receptor in the sample can be combined with the detection of another specific tumor marker to confirm that the cancer is the specific type of cancer.

By "diagnosed" is meant that one skilled in the art has determined either by blood test, immunoassay, ultrasound, urinalysis, magnetic resonance imaging, physical examination, biopsy or any other diagnostic method that the patient has cancer.

The invention further provides a method of classifying a cancer as a colorectal cancer comprising, obtaining a sample from a patient diagnosed with cancer, contacting the sample with a Mob-5 receptor antigen, and detecting the binding of the antigen with a Mob-5 receptor antibody in the sample, wherein the binding of the antigen to the antibody indicates the cancer is a colorectal cancer, thereby classifying the cancer as a colorectal cancer. The detection of binding of Mob-5 antigen to Mob-5 receptor antibody in the sample can be accomplished by utilizing immunological detection methods previously discussed.

The invention further provides a method of detecting Mob-5 receptor antibody in a sample comprising contacting a sample with a Mob-5 receptor antigen, and detecting the binding of the antigen with a Mob-5 receptor antibody in the sample, wherein the binding of the antigen to the antibody indicates the presence of Mob-5 receptor antibodies in the sample.

The presence of Mob-5 receptor antibodies in a sample could be utilized to detect autoimmune disorders such as inflammatory bowel disease, multiple sclerosis, rheumatoid arthritis, diabetes mellitus, pernicious anemia, autoimmune gastritis, psoriasis, Bechet's disease, idiopathic thrombocytopenic purpura, Wegener's granulomatosis, autoimmune thyroiditis, autoimmune oophoritis, bullous pemphigoid, pemphigus, polyendocrinopathies, Still's disease, Lambert-Eaton myasthenia syndrome, myasthenia gravis, Goodposture's syndrome, autoimmune orchitis, autoimmune uveitis, systemic lupus erythematosus, Sjogren's syndrome and ankylosing spondylitis.

The present invention is more particularly described in the following examples which are intended as illustrative only since numerous modifications and variations therein will be apparent to those skilled in the art.

EXAMPLES

Cell Lines and Culture

All cell lines including 293T, HaCaT and BHK (from ATCC) were grown in Dulbecco's Modified Eagle Medium (DMEM) (Life Technologies Inc. Grand Island, N.Y.) with 10% fetal bovine serum (HyClone, Logan, Utah) and 1% penicillin-streptomycin (Life Technologies Inc. Grand Island, N.Y.) at 37° C. with 10% $CO_2$ Cos-E5, a clonally purified Cos-1 cell line, was maintained in DMEM with 10% Bovine calf serum and 1% penicillin-streptomycin.

RNA Purification, RT-PCR and Southern Blot Hybridization

Total RNA from human cancer tissues or cultured cells was purified using the RNApure reagent following the manufacturer's instructions (GenHunter Corp., Nashville, Tenn.). The cDNA synthesis, RT-PCR and southern blot hybridization were carried out as described previously (7). The method for quantitative analysis of human IL-24 mRNA by competitive RT-PCR was essentially according to the method described previously (23). First, a competitive IL-24 cDNA template with 91 bp deletion from the native cDNA sequence was constructed by PCR with primers LhMob-4 (5'-TGCAAAGCCTGTGGACTTTAGCCAGGTATCAG-3') (SEQ ID NO: 8) and RhMob5-2 (5'-CCGCCTGTGTGCACTGTCTCTGATG-3') (SEQ ID NO: 9). The resulting 397 bp competitor PCR product was cloned into the PCR-TRAP cloning vector (GenHunter Corp., Nashville, Tenn.). The cloned IL-24 competitor cDNA was purified and the same amount of an optimal concentration of the competitor template was included in each RT-PCR reaction using primers LhMob3 (5'-TGCAAAGCCTGTGGACTTTAGCCAG-3') (SEQ ID NO: 12) and RhMob5-2. The signal of the 488 bp native IL-24 PCR product was separated from that of the 397 bp competitor by 1.5% agarose gel electrophoresis.

Production of Secreted AP, IL-24-AP Fusion Proteins and His-tagged IL-24 (IL-24-His)

Production of secreted AP and IL-24-AP fusion proteins were described previously (7, 24). For the production of human IL-24-His, the PCR primer was used to attach 9×His to the C terminus of IL-24, and the resulting PCR product was subcloned into the Bgl II site of the pAPtag-5 expression vector (GenHunter Corp., Nashville, Tenn.). After transfecting into the 293T cells, stable cell lines constitutively secreting IL-24-His into the conditioned medium were obtained.

AP and IL-24-AP Binding and Cell Staining Assays

Receptor binding studies using AP activity and in situ cell staining assays were carried out using AP assay reagent A and AP assay reagent S, respectively (GenHunter Corp., Nashville, Tenn.), following manufacture's instruction as previously described (7).

Antibody Preparation and Immunoblotting

The polyclonal antibody to human IL-24 was described previously (7). For monoclonal antibody production, bacterially expressed human IL-24-6×His (7) was purified as a denatured protein. After dialysis in PBS, 25–100 μg of recombinant protein in Fruend's complete adjuvant was injected into 4–5 week old female Balb/C mice. After three weeks, sera from immunized mice were assayed by ELISA for the titer of anti-IL-24 antibody, using human IL-24-AP as an antigen as well as a reporter. Mice were then boosted with an additional 25–100 µg of purified human IL-24-AP fusion protein in order to enhance the production of antibodies recognizing native, rather than, denatured IL-24. Three days prior to fusion, mice were hyper-immunized, again with 25–100 µg of IL-24-AP. Spleens from hyper-immunized mice were then fused with SP2/O myeloma cells and hybridomas producing anti-Mob5 specific hybridomas were subcloned according to standard procedures.

Deglycosylation

IL-24-His was partially purified from the conditioned medium using Ni-NTA beads (Qiagene). Deglycosylation of IL-24-His was carried out with endoglycanase F (PNGase F) (Roche Molecular Chemicals) following a previously described procedure (25).

Purification of PBMCs and Induction of IL-24 by Concanavalin A (ConA)

Human PBMCs were freshly purified from healthy donors by gradient centrifugation using LSM lymphocyte separation medium (ICN, Costa Mesa, Calif.) according to manufacturer's instruction. After resuspended in RPMI medium containing 10% FBS, the cells was stimulated with either bacterial lipopolysacharide LPS (100 ng/mL) or ConA (25 µg/mL) for 2 and 4 hours. Following the treatment, the conditioned media were analyzed for IL-24 production by western blot analysis as described (7) using a monoclonal antibody to human IL-24 (clone L14).

Transfection and Gel-Shift Assay

The coding regions of human IL-10R2, IL-20R2 and IL22-R1 were PCR amplified and subcloned between the Kpn I and Xba I sites of the expression vector pcDEF3. The complete coding region of human IL-20R1 was PCR amplified using an EST clone (IMAGE # 2700520) (ATCC, Manassas, Va.) as a template and subcloned into the Bgl II site of the pAPTag-5 expression vector. Expression plasmids encoding different receptor subunits were transiently transfected into either Cos-E5 or BHK cells using FUGENE-6 (Roche Molecular Chemicals) according to manufacturer's instruction. Two days after transfection, cells were treated with 1:10 dilution (directly into the existing culture media) of the 293T conditioned medium either without or with IL-24-His (final concentration at about 50 ng/mL). Thirty minutes following the treatment, nuclear extracts were prepared by the standard protocol. For STAT specific gel-shift assays, STAT-specific double stranded DNA probe GRR (5'-ATGTATTTCCCAGAAA-3' (SEQ ID NO: 10)/5'-CCTTTTCTGGGAAATAC (SEQ ID NO: 11)-3') was end labeled with $^{32}P$, incubated with nuclear extracts and separated on 5–6% non-denaturing polyacrylamide gels as described previously (3). For super-shift experiments, 1 µg of STAT-1 or STAT-3 specific antibody was used (Santa Cruz).

LPS Induced TNF-α Production from PBMCs

Freshly prepared PBMCs (see above) were resuspended in RPMI plus 10% FBS and equal aliquots (150 µL) were plated in a 96-well plate. LPS was then added to each well at a final concentration of 80 ng/mL in the absence or presence of either 20 ng/mL of recombinant human IL-10 (R&D Systems, Minneapolis, Minn.) or 100 ng/mL of human IL-24-His, or both for five hours. TNF-α levels in the conditioned media of the cells were determined with an ELISA kit for human TNF-α (R&D Systems, Minneapolis, Minn.) as instructed by the manufacturer.

Overexpression of IL-24 in Human Colon Cancer

To determine the relevance of IL-24 expression in human cancer is of great importance for the present invention's model system for ras-mediated cell transformation (7). To evaluate the expression of IL-24 in colorectal cancer which has frequent mutations in the ras proto-oncogene, quantitative RT-PCR analysis with RNA isolated from the tumors and the adjacent normal tissues from five colorectal cancer patients was carried out (FIG. 1A, upper panel). The quantitative RT-PCR results were also confirmed by regular RT-PCR of the entire coding region of IL-20 followed by Southern blot using human IL-24 cDNA as a probe (FIG. 1A, middle panel). These results showed that IL-24 expression was confined to cancer tissues from five out five patients, with patient No. 5 expressing IL-24 at a much higher level.

Induction of IL-24 by Activated T Cells

Although IL-24 expression in rodents was not detectable in any normal adult tissues or in embryos (7), it was reported by others that the gene appeared to be induced under pathological conditions such as wound healing (6). Given the fact that IL-24 belongs to the IL-10 family of cytokines which can be induced by ConA activated T cells (11, 25), IL-24 induction under such conditions was analyzed. Freshly prepared human PBMCs were stimulated with either bacterial LPS or Con A. Following stimulation, the production of IL-24 in the conditioned media was analyzed by Western blot (FIG. 1B). ConA, which causes mostly T cell activation, induced a rapid secretion of IL-24 by the PMNCs. LPS, on the other hand, had little effect on IL-24 production.

IL-24 is a Glycosylated Protein

Figure 2:
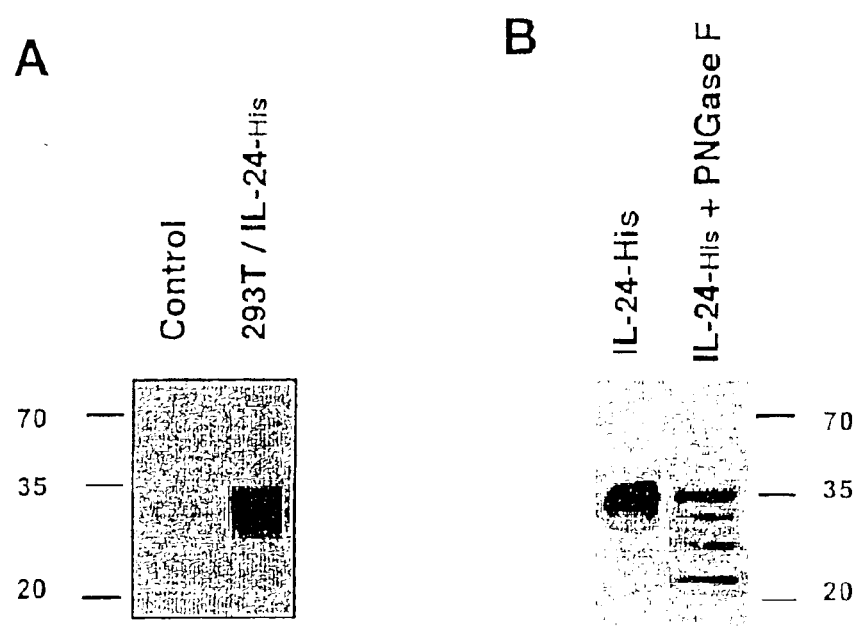
FIG. 2A shows that conditioned media of 293T and 293T stably transfected with the IL-24-His expression vector were analyzed by Western blot using a IL-24 specific antibody.
FIG. 2B shows the glycosylation of human IL-24. The partially purified IL-24-His before and after treating with endoglycanase F (PNGase F) were analyzed by Western blot using a monoclonal antibody specific to IL-24. Several bands smaller that the untreated IL-24-His were seen after digestion with PNGase F, indicating that IL-24-His is indeed glycosylated.

The predicted molecular weight of human IL-24 is 23.8 kDa, but the IL-24 secreted by either human PBMCs (FIG. 1B) or IL-24-His secreted by 293T stable transfectants appeared to be much bigger with a molecular weight closer to 35 kDa (FIG. 2). To determine whether this is due to glycosylation, partially purified IL-24-His was subjected to digestion by endoglycanase F (PNGase F). As predicted, the deglycosylating enzyme converted the 35 kDa form of IL-24-His to several smaller molecular weight forms, with the lowest band being close to 23 kDa (FIG. 2B). The presence of bands of intermediate sizes could be due to an incomplete deglycosylation. This result suggests that IL-24 is extensively glycosylated.

Identification of the IL-24 Receptors

Since IL-24 shares significant homology to IL-10, it was predicted that IL-24 is a member of the IL-10 family of cytokines (7). Supporting this hypothesis is the finding of this group that not only IL-24, but also its putative cell surface receptor appears to be induced by ras oncogenes (7). Shortly after the initial description of IL-24, two more IL-10 family of cytokines, IL-20 and IL-22, and their receptors were reported (9–10). Sequence alignment indicated that IL-24 and the other members of the IL-10 family of cytokines share an overall homology ranging from 24–33% among each other. Among them, IL-24 is closest to IL-20 with 33% homolgy overall, and the highest homology is found at the C-termini of the proteins.

Based on published data and database searches of GenBank (NCBI), only three R1 and two R2 types of the IL-10 family of receptor subunits can be identified. The three R1 subunits are IL-10R1, IL-20R1 and IL-22R1, whereas the two R2 subunits are IL-20R2 and IL-10R2, the latter of which is also the second receptor subunit for IL-22. Thus, the IL-24 receptor could be a heterodimer of a combination of the known R1 and R2 receptors. To determine if IL-24 is the ligand for any of the heterodimers of known R1 and R2 receptors, receptor binding assays were carried out using either secreted human placental alkaline phosphatase (AP) or the IL-24-AP fusion protein as a probe (FIG. 3A; 7). The quantitative cell surface binding assays were carried out with Cos cells after transfecting plasmids over-expressing IL-10R2, IL-20R1, IL-22R1 and IL-20R2 individually or in all four R1/R2 combinations (FIG. 3B). IL-24-AP, but not AP, exhibited significant binding to Cos cells transfected with IL-20R2 alone, and the binding was further dramatically increased when IL-20R2 was co-transfected with either IL20-R1 or IL-22R1. Neither IL20-R1 nor IL-22R1 alone was able to bind to IL-24-AP. Using AP staining assays, the quantitative IL-24-AP binding data was confirmed (FIG. 3C). Specific cell surface staining was detected with IL-24-AP when Cos cells were transiently transfected with IL-20R2, but not IL-20R1 or IL-22R1 alone (FIG. 3C). When cells were transiently transfected with IL-20R2 in combination with either IL-20R1 or IL-22R1, the cell surface binding of IL-24-AP was greatly increased (FIG. 3C). In addition to increased ability to bind IL-24-AP, the presence of either R1 subunit resulted in a much more uniformed distribution of the heterodimeric receptor over the entire cell surface (FIG. 3C).

Figure 3:
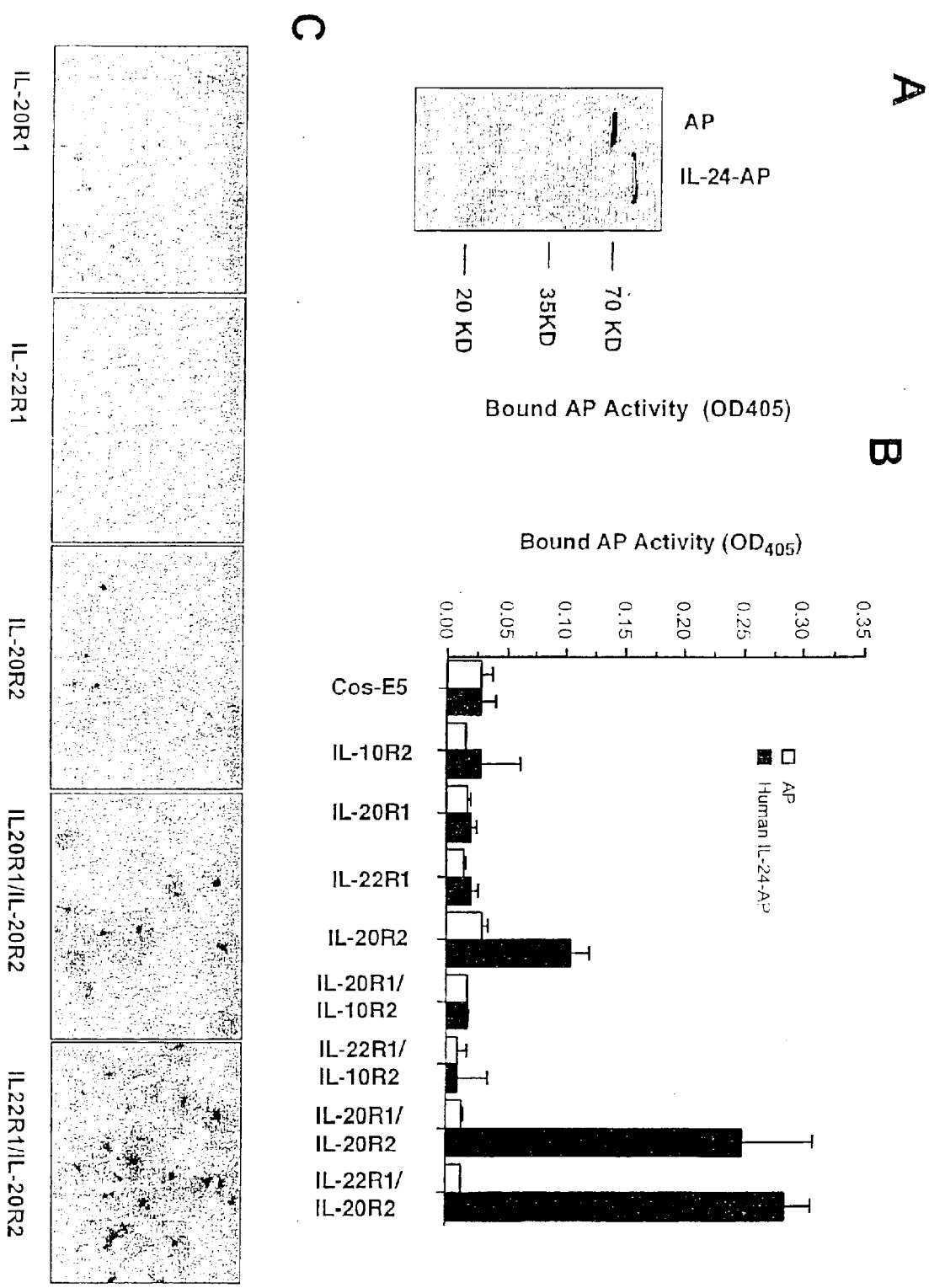
FIG. 3A illustrates western blot analysis of conditioned media containing alkaline phosphatase (AP) or IL-24-AP, using polyclonal antibody against AP. These media were used to conduct the following IL-24 receptor binding studies.
FIG. 3B shows the receptor binding analysis for IL-24. Cos-E5 cells (a clonally purified Cos-1) were transiently transfected with expression vectors (individually or in pair) encoding the corresponding receptor subunits as indicated. The cells with and without transfection were subsequently assessed for their ability to bind IL-24-AP (solid bars) versus AP control (open bars). None of the receptor subunits alone, except IL-20R2, exhibited appreciable IL-24-AP specific binding, which was substantially potentiated when either IL-20R1 or IL-22R1 was co-transfected with IL-20R2.
FIG. 3C illustrates cell surface staining assay for the IL-24 receptor binding. Cos-E5 cells transfected with either the IL-20R1, IL-22R1 and IL20R2 expression vector alone or in pairs were stained for the cell surface-bound IL-24-AP activity and viewed under a light microscope (20× magnification) without phase contrast. The result was consistent with that obtained from the quantitative binding study, in that, cells transfected with both IL-20 receptor (IL-20R1/IL-20R2) heterodimeric receptor exhibited positive staining by IL-24-AP. While cells transfected with IL-20R2 alone also showed weak staining for IL-24 AP, neither IL-20R1 nor IL22R1 was able to confer IL-24AP binding to the cells.
Figure 4:
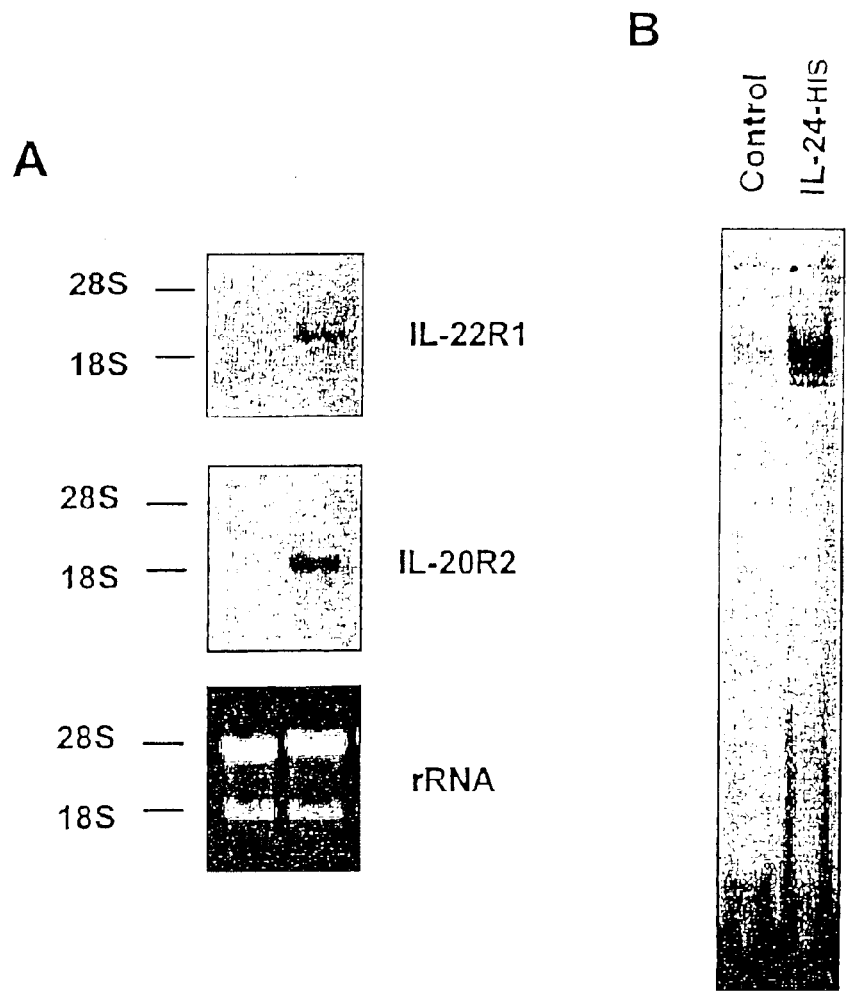
FIG. 4A is a northern blot analysis showed that HaCaT human keratinocytes are positive for IL-22R1/IL-20R2 receptor expression. Unlike HaCaT cells, BHK cells do not express either receptor subunit.
FIG. 4B shows IL-24 dependent STAT activation in HaCaT cells. HaCaT cells were stimulated for 30 minutes with either 293T control medium or IL-24-His conditioned medium, and then processed for gel-shift assay for STAT activation using a $^{32}$P-labled STATs' specific probe (GRR).

IL-24 Signals through both the IL-20 Receptor (IL20R1/IL-20R2) and IL22R1/IL-20R2 Heterodimers To functionally determine if IL-24 can signal through these putative receptors by activating the downstream JAK-STAT pathways, as has been observed for other members of the IL-10 family of cytokines, the following three experiments were performed. First, the expression of IL-22R1 in a human keratinocyte cell line, HaCaT, which was shown to be positive for IL-20 receptor (IL20R1/IL-20R2) was examined (Blumberg, et al., 2001). The finding of the co-expression of IL-22R1 and IL-20R2 in the HaCaT, but not BHK cell line (FIG. 4A), suggests that the former could contain both receptors that are capable of binding IL-24. The gel-shift assays were then conducted for the functional analysis of STAT activation in the HaCaT cells by IL-24-His (FIG. 4B). After 30 min stimulation, IL-24-His treated cells showed a marked increase in STAT activation (FIG. 4B). It was possible that the IL-24 induced STAT activation in HaCaT cells could be due to IL-24 binding to either the IL-20 receptor or to IL-22R1/IL-20R2. To differentiate between these two possibilities, vectors expressing IL-20R1 and IL20R2, or IL-22R1 and IL-20R2 were transfected into the BHK cell line, which does not have endogenous IL-24 receptors as predicted by the lack of IL-20R2 expression. Interestingly, upon stimulation of the transfected cells with either the control- or IL-24-His-conditioned medium, the gel shift assay revealed that both the IL-20 receptor (IL20R1/IL-20R2) and IL-22R1/IL-20R2 heterodimeric receptor were able to confer comparable and robust IL-24 dependent STAT activation (FIG. 5A). None of the receptor subunits alone, including IL-20R2, was able to confer IL-24 dependent STAT activation. These data are consistent with the receptor binding assays (FIG. 3). Finally, to determine which STAT was activated by IL-24 in BHK cells transfected with the IL-24 receptor (IL-22R1/IL-20R2), antibodies against different STATs were used to interfere with the gel-shift assays. A higher resolution band-shift gel showed that IL-24 binding to its heterodimeric receptor led to the activation of both STAT-1 and -3, which could be interfered (for STAT-1) or super-shifted (for STAT-3) by the corresponding antibodies, respectively (FIG. 5B).

Effect of IL-24 on LPS Induced TNF-α Production

Figure 5:
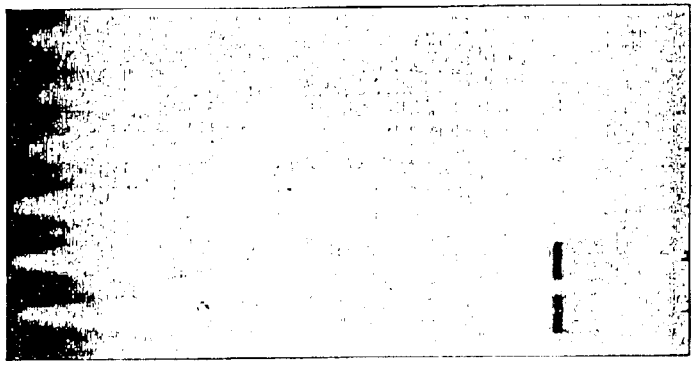
FIG. 5A shows that IL-24 signals through both heterodimeric receptors of IL-20 (IL20R1/IL-20R2) and IL22R1/IL20R2 by activating STAT-1 and STAT-3. BHK cells were transiently transfected with the receptor pairs as indicated. After stimulating the cells with either the control 293T medium or 293T/IL24-His medium for 30 min, STAT activation was analyzed by a 6% polyacrylamide gel with nuclear extracted from the cells using the $^{32}$P-labled GRR probe. IL-24-His was able to confer specific activation of STATs through both IL-20R1/IL-20R2 and IL22R1/IL20R2 heterodimeric receptors.
FIG. 5B illustrates that IL-24 signals through its receptors by activating both STAT-1 and -3. BHK cells transiently transfected with IL22R1/IL20R2 expression vectors were stimulated with either the 293T control medium or IL-24His-293T medium for 30 min. Gel-shift assays were carried out with nuclear extracts using the 32P-labeled GRR probe in the absence or presence of antibodies against STAT-1 and STAT-3 as indicated. A 5% polyacrylamide gel was used for better separation of different forms of STAT-GRR complexes. Both STAT-1 and STAT-3 antibodies caused either disruption (STAT-1) or super-shift (STAT-3, indicated by arrowhead) of STAT-GRR complexes induced by IL-24-His, respectively.
Figure 5:
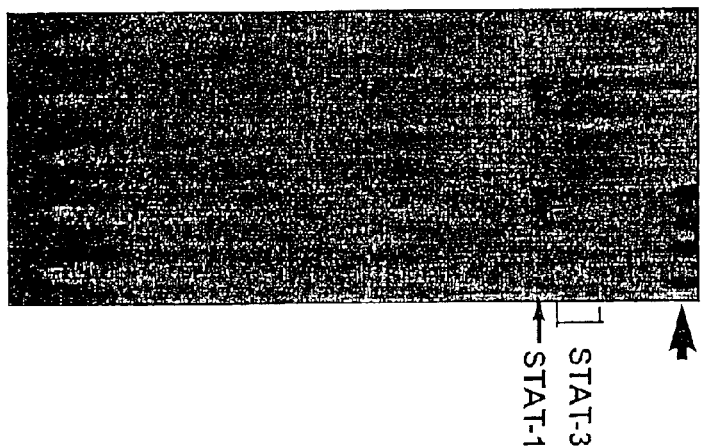
Figure 6:
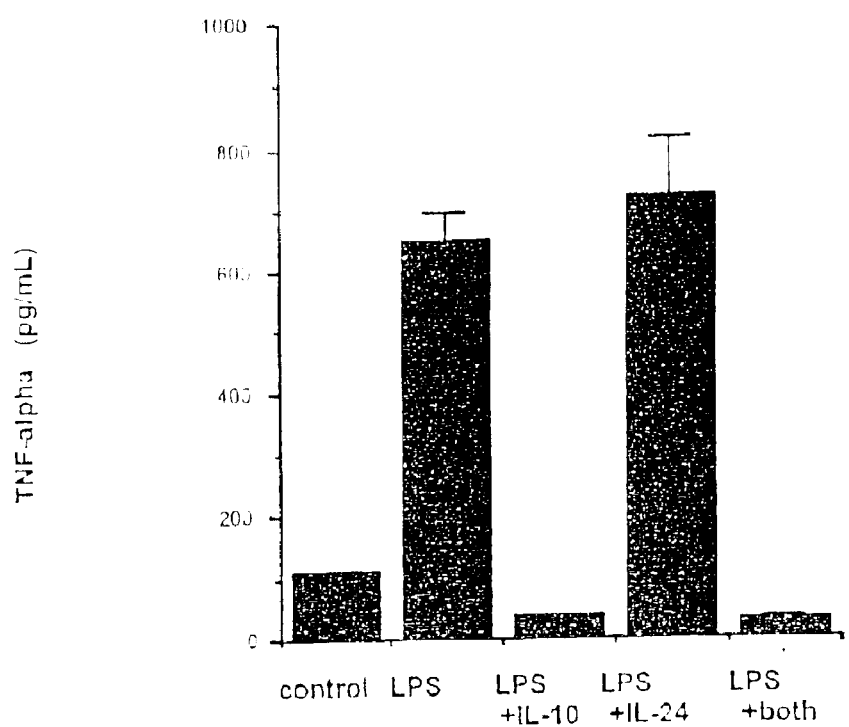
FIG. 6 shows the inability of IL-24 to inhibit LPS induced TNF-α production from PBMCs. The freshly prepared human PBMCs were either mock treated or treated with 80 ng/mL LPS for 4 hours in the absence and presence of IL-10 (20 ng/mL), IL-24-His (100 ng/mL) or both cytokines as indicated. TNF-α secreted into the media was quantified by ELISA. Unlike IL-10, IL-24-His had little inhibitory effect on LPS induced TNF-α production by PBMCs.

IL-10 is known to be a potent inhibitor of cytokine synthesis induced by LPS (27). To determine if IL-24 has a similar biological activity, freshly prepared human PBMCs were stimulated with LPS in the absence or presence of IL-10, IL-24 or both. The effects of IL-10 and IL-24 on LPS induced TNF-α production were determined by ELISA. Unlike IL-10, IL-24 did not appear to have any inhibitory effect on TNF-α induction by PBMCs (FIG. 5).

Induction of One of the IL-24 Receptors, IL-20 Receptor, by Ha-ras Oncogene

Figure 7:
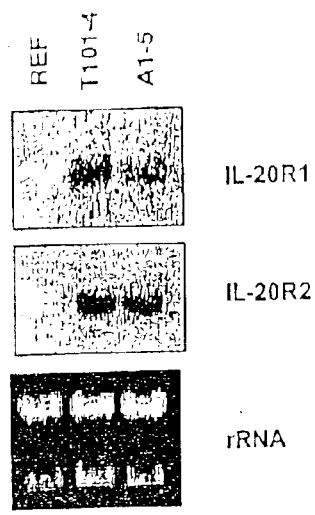
FIG. 7 shows the induction of IL-24 receptor (IL-20R1/IL-20R2) by Ha-ras oncogene. In these experiments REF cells before and after transformation by oncogenic H-ras and mutant p53 (cell lines T101-4 and A1-5) were analyzed by Northern blot for the expression of both IL-20 subunits.

Previous results showed ras oncogenes can activate not only IL-24, but also its cell surface receptor(s) (Zhang et al., 2000). An EST data base search revealed several cDNA matches to both rodent IL-20R1 and IL-20R2, but not IL-22R1, Using these cDNAs as probes, we showed that compared to the parental primary rat embryo fibroblasts (REF), REF transformed by oncogenic Ha-ras and mutant p53 (Martinez, 1991), had overexpression of not only IL-24, but also IL-20 receptor (IL-20R1/IL-20R2, which is also the second IL-24 receptor) (FIG. 7). This result shows that ras oncogenes can activate IL-24/IL-24Rs autocrine loops. It should be noted that Rat-1 cells transformed by Ha-Ras also had an elevated expression of IL-20 receptor, which is lower, however, than that found in T101-4 and A1-5 cells. It is possible that the inactivation of p53 could further enhance the ras activation of IL-24/IL-24R autocrine loop. By utilizing the rodent cDNA for IL-22R1, one of skill in the art can determine if the other IL-24 receptor (IL-22R1/IL20R20) is also activated by ras oncogenes.

When treated with ha-RAS inhibitor FTI, T101-4 cells showed rapid decrease in IL-20R2 expression. In contrast, MAPK kinase inhibitor, PD98059 had less effect. This result re-enforces that ras oncogenes, through multiple pathways, can activate an IL-24/IL-24R autocrine loop. It should be noted that Rat-1 cells transformed by Ha-Ras also had an elavated expression of IL-20 receptor which is lower, however, than that found in T101-4 and A1-5 cells It is possible that the inactivation of p53 could further enhance the ras activation of IL-24/IL-24R autocrine loop.

IL-24 Signaling Pathway can Support Cell Survival and Proliferation

In order to understand the functions of IL-24 with a clear readout in cell survival and proliferation, an IL-3 dependent murine pro-B cell line, Ba/F3 was utilized (Rodriguez-Tarduchy et al. 1990 (30), 1990; Devireddy et al., 2001 (31)). This cell line depends on IL-3, in addition to fetal bovine serum, for survival and growth. Upon IL-3 withdraw, Ba/F3 cells undergo rapid apoptosis within 24 hours (Rodriguez-Tarduchy et al., 1990 (30)).

After stably expressing either of the IL-24 receptors in Ba/F3 cells (pooled G418 resistant clones), which were confirmed by ligand binding, it was determined whether or not IL-24 could substitute IL-3 in supporting cell viability and growth. Using a cell viability assay with Alama Blue dye (Liu et al., 1994), IL-24 was shown to be able to prevent cell death in an IL-24 receptor-specific manner. The result was also confirmed by apoptosis assay for chromosomal DNA fragmentation as reported previously (Rodriguez-Tarduchy et al., 1990). Because the cell viability assay could not tell living cells from growing ones, IL-24 dependent cell growth was measured. Ba/F3 cells transfected with vector alone were obligatorily IL-3 dependent whereas Ba/F3 cells transfected with the either of the IL-24 receptors could depend on either IL-3 and IL-24 for long term proliferation.

These functional results for IL-24 provide strong evidence that an IL-24 autocrine (or paracrine) loop plays a key role in mediating a ras oncogene effect in supporting both tumor cell survival and proliferation.

Colon Cancer Cell Line, SW480, is Positive for IL-24 Receptor(s)

Figure 8:
FIG. 8 shows that colon cancer cell line, SW480 is positive for IL-24 receptor(s). The SW480 cells were stimulated with either 293T control medium or IL-24-His conditioned medium for 30 min. STAT activation was then analyzed by a gel-shift assay. The arrowhead indicates IL-24 specific STAT activation.

To obtain more evidence for the presence of IL-24 receptor in human cancer cells, a colon cancer cell lines SW480, which was shown to contain both mutations in Ka-ras and p53 was examined. Stimulation of the cells with recombinant IL-24 led to increase in STAT activation as determined by gel-shift assay (FIG. 8).

The identification of two functional IL-24 receptors, one consisting of two recently identified class II cytokine receptors, IL-22R1 and IL-20R2, the other being the IL-20 receptor (IL-20R1/IL-20R2), shows that IL-24 is indeed a new member of IL-10 family of cytokines, following IL-20 and IL-22. The observation that Mob-5-AP exhibited nearly identical properties to that of human IL-24-AP in receptor binding studies presented in FIG. 3, shows that Mob-5 and Mda-7 are the rat and human homologs of IL-24, respectively.

The three previously known receptors of the IL-10 family of cytokines are all heterodimeric, each being made up of a R1 type and a R2 type of receptor subunit, IL-10 and IL-22 share the same R2 type of receptor subunit, IL-10R2. This invention shows that IL-24 not only shares the same R2 type of receptor subunit with that of IL-20, but also its R1 type of receptor subunit is shared with that of IL-22. The discovery of such a scheme of receptor subunit swapping is important in two aspects. First, there could be a total of six combinations of heterodimeric receptors made up of three known R1 and two known R2 receptor subunits, to which four combinations now have already assigned ligands, IL10, IL-20, IL-22 and IL-24 (Table I). Thus, two more receptors made up of IL10R1/IL20R2 and IL-20R1IL10R2 have yet to be assigned with their corresponding ligands. These may correspond with two more IL-10 like cytokines that do now have known receptors, IL-19 (8) and AK155 (4), both of which are encoded by cellular genes. The receptor-ligand relationship presented in this invention will be helpful for the identification and assignment of other receptors and their corresponding ligands.

Second, the scheme of receptor subunit swapping of the present invention shows that there is crosstalk among IL-10 family of cytokines (10). Clearly shown by this study, both IL-20 and IL-24 can signal through the same IL-20 receptor. Conversely, IL-20 may also be able to signal through the other new IL-24 receptor (IL-22R1/IL-20R2). Moreover, the finding that IL-22R1 is the first R1 type of receptor subunit shared by two different ligands of the IL-10 family of cytokines, would also predict a potential crosstalk between IL-22 and IL-24. For example, although the studies presented herein showed that IL-24 could not signal through the IL-22 receptor (IL-22R1/IL-10R2), IL-22 may be able to signal through the IL-24 receptor(s). Such potential crosstalk among IL-10 family of cytokines and their receptors can now be readily tested as a result of the present invention.

Dysfunction in the control of such ligand-receptor crosstalk as a result of aberrant expression of the cytokines and their receptors could be one of the underlying causes for diseases, such as cancer. The present invention shows that ras oncogenes cause constitutive expression of IL-24 in cells from non-hematopoietic origin (7). Ras transformed rat embryo fibroblasts and intestinal epithelial cells not only constitutively produce IL-24, but also have increased expression of the IL-24 receptor(s) (7). Like IL-20, one of the likely normal target tissues for IL-24 is skin, since the human keratinocyte cell line HaCaT appears to express both endogenous IL-24 receptors. This is also consistent with the finding that IL-24 is transiently expressed in lesions of skin injury from a rat wound-healing model (6). It should be pointed out that the human IL-24 gene (mda-7), when ectopically expressed, was reported to have marginal growth inhibitory effect on some cancer cell lines (29), which is in paradox with our finding that the gene is both induced by ras oncogene and overexpressed in colon cancer tissues. While little expression of IL-22R1 was detected from colon and lung, over-expression of the gene was found in cancer cell lines from these tissue origins (10). Virally encoded IL-10 like cytokines may participate in cell infection and transformation, and act through Il-24 receptor(s).

Throughout this application, various publications are referenced. The disclosures of these publications in their entireties, as well as the references cited in these publications, are hereby incorporated by reference into this application in order to more fully describe the state of the art to which this invention pertains.

References

1. Moore, K. W., O'Garra, A., de Waal Malefyt, R., Vieira, P., and Mosmann, T. R. (1993) *Annu. Rev. Immunol.* 11, 165–190.
2. Dumoutier, L., Louahed, J., and Renauld, J. C. (2000) *J. Immunol.* 164, 1814–1819.
3. Dumoutier, L., Van Roost, E., Colau, D., and Renauld, J. C. (2000) *Proc, Natl. Acad. Sci. U.S.A.* 97, 10144–10149.
4. Knappe, A., Hor, S., Wittmann, S., and Fickenscher, H. (2000) *J. Virol.* 74, 3881–3887.
5. Jiang, H., Lin, J. J., Su, Z., Goldstein, N. I., and Fisher, P. B. (1995) *Oncogene* 11, 2477–2486.
6. Soo, C., Shaw, W. W., Freymiller, E., Longaker, M. T., Bertolami, C. N., Chiu, R., Tieu, A., and Ting, K. (1999) *J. Cell. Biochem.* 74, 1–10.
7. Zhang, R., Tan, Z., and Liang, P. (2000) *J. Biol. Chem.* 275, 24436–24443.
8. Gallagher, g., Dickensheets, H., Eskadale, J., Izotova, L. S., Mirochnitchenko, O. V., Peat, J. D., Peska, S., Vazquez, N., donnelly, R. P., and Kotenko, S. V. (2000) *Genes Inmmun.* 1, 442–450.
9. Blumberg, H., Conklin, D., Xu, W. F., Grossmann, A., Brender, T., Carollo, S., Eagan, M., Foster, D., and Haldeman, B. A., Hammond, A., Haugen, H., Jelinek, L., Kelly, J. D., Madden, K., Maurer, M. F., Parrish-Novak, J., Prunkard, D., Sexson, S., Sprecher, C., Waggie, K., West, J., Whitmore, T. E., Yao, L., Kuechle, M. K., Dale, B. A., and Chandrasekher, Y. A. (2001) *Cell* 104, 9–19.
10. Kotenko, S. V., Izotova, L. S., Mirochnitchenko, O. V., Esterova, E., Dickensheets, H., Donnelly, R. P., and Pestka, S. (2001) *J. Biol. Chem.* 276, 2725–2732
11. Xie, M. H., Aggarwal, S., Ho, W. H., Foster, J., Zhang, Z., Stinson, J., Wood, W. I., Goddard, A. D., and Gurney, A. L. (2000) *J. Biol. Chem.* 275, 31335–31339
12. Liu, Y., Wei, S. H.-Y., Ho, a. S.-Y., de Waal Malefyt, R., and Moore, K. W. (1994) *J. Immunol.* 152, 1821–1829.
13. Kotenka, S. V., Krause, C. D., Izotova, L. S., Pollack, B. P., Wu, W., and Pestka, S. (1997) *EMBO J.* 16, 5894–5903.
14. Kotenko, S. V., and Pestka, S. (2000) *Oncogene* 19, 2557–2565
15. Liang, P., and Pardee, A. B. (1992) *Science* 257, 967–971.
16. Liang, P., L. Averboukh, W. Zhu, and Pardee, A. B. (1994) *Proc. Natl. Acad. Sci. U. S. A.*, 91, 12515–12519.
17. Zhang, R., Zhang, H., Zhu, W., Coffey, R., Pardee, A. B., and Liang, P. (1997) *Oncogene* 14, 1607–1610.
18. Jo, H., Zhang, R., Zhang, H. McKinsey, T. A. Ballard, D. W. and Liang, P. (2000) *Oncogene* 19, 841–849.
19. Jo, H., Cho, Y., Zhang, H. and Liang P. (2001) *Methods in Enzymol.* (Academic Press) 332, 233–244.

20. Miyazaki, I., Cheung, R. K., and Dosch, H. M. (1993) *J. Exp. Med.* 178, 439–447.
21. Kotenko, S. V., Saccani, S., Izotova, L. S., Mirochnitchenko, O. V., and Pestko, S. (2000) *Proc. Natl. Acad. Sci. U.S.A.* 97, 1695–1700.
22. Lee, H. J., Essani, K. and Smith, G. L. (2001) J. Virol. 281,170–192.
23. Celi, F. S., Zenilman, M. E., and Shuldiner, A. R. (1993) *Nucleic. Acids. Res.* 21, 1047.
24. Flanagan, J. G., and Leder, P. (1990) *Cell* 63: 185–194.
25. Tan, J. C., Braun, S., Rong, H., DiGiacomo, R., Dolphin, E., Baldwin, S., Narula, S. K., Zavodny, P. J., and Chou, C. C. (1995) *J. Biol. Chem.* 270, 12906–12911.
26. Moore, K. W., Vieira, P., Fiorentino, D. F., Trounstine, M. L., Khan, T. A., and Mosmann, T. R. (1990) *Science* 248, 1230–1234.
27. Wang, P., Wu, P., Siegel, M. I., Egan, R. W., and Billah, M. M. (1994) *J. Immunol.* 153, 811–816.
28. Schaefer, g., Venkataraman, V. and Schindler, U. (2001) *J. Immunol.* 166, 5859–5863.
29. Jiang, H., Su, Z., Lin, J. J., Goldstein, N. I. Young, C. S. H., and Fisher, P. B. (1996) *Proc. Natl. Acad. Sci. USA.* 93, 9160–9165.
30. Rodriguez-Tarduchy et al. "Regulation of apoptosis in interleukin-3-dependent hemopoietic cells by interleukin-3 and calcium ionophores" *EMBO J.* 1990 Sep. 9(9):2997–3002.
31. Devireddy et al. "Induction of apoptosis by a secreted lipocalin that is transcriptionally regulated by IL-3 deprivation" *Science.* 2001 Aug. 3;293(5531):829–34.

What is claimed is:

1. An isolated composition comprising a complex between human IL-22R1 and human IL-20R2.

2. A vector comprising a nucleic acid encoding human IL-22R1 and human IL-20R2.

3. The vector of claim 2 in a host suitable for expressing the nucleic acid.

4. A cell containing an exogenous nucleic acid encoding IL-22R1 and IL-20R2 on the same or on different transfection vectors.

* * * * *

SEQUENCE LISTING

```
<160> NUMBER OF SEQ ID NOS: 12

<210> SEQ ID NO 1
<211> LENGTH: 226
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 1

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220
```

Arg Thr
225

<210> SEQ ID NO 2
<211> LENGTH: 229
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 2

Met Gln Thr Phe Thr Met Val Leu Glu Glu Ile Trp Thr Ser Leu Phe
1               5                   10                  15

Met Trp Phe Phe Tyr Ala Leu Ile Pro Cys Leu Leu Thr Asp Glu Val
            20                  25                  30

Ala Ile Leu Pro Ala Pro Gln Thr Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu
225

<210> SEQ ID NO 3
<211> LENGTH: 248
<212> TYPE: PRT
<213> ORGANISM: Artificial Sequence
<220> FEATURE:
<223> OTHER INFORMATION: Description of Artificial Sequence; Note =
      Synthetic Construct

<400> SEQUENCE: 3

Met Arg Ala Pro Gly Arg Pro Ala Leu Arg Pro Leu Pro Leu Pro Pro
1               5                   10                  15

Leu Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
        35                  40                  45

-continued

```
Asn Met Lys Asn Val Leu Gln Trp Thr Pro Pro Glu Gly Leu Gln Gly
         50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
            100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
            130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
            195                 200                 205

Glu Pro Asn Thr Leu Tyr Cys Val His Val Glu Ser Phe Val Pro Gly
            210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys
                245

<210> SEQ ID NO 4
<211> LENGTH: 2795
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 4
gggagggctc tgtgccagcc ccgatgagga cgctgctgac catcttgact gtgggatccc      60
tggctgctca cgcccctgag gacccctcgg atctgctcca gcacgtgaaa ttccagtcca     120
gcaactttga aaacatcctg acgtgggaca gcgggccaga gggcaccccca gacacggtct     180 acagcatcga gtataagacg tacggagaga gggactgggt ggcaaagaag ggctgtcagc     240
ggatcacccg gaagtcctgc aacctgacgg tggagacggg caacctcacg gagctctact     300
atgccagggt caccgctgtc agtgcgggag gccggtcagc caccaagatg actgacaggt     360
tcagctctct gcagcacact accctcaagc cacctgatgt gacctgtatc tccaaagtga     420
gatcgattca gatgattgtt catcctaccc ccacgccaat ccgtgcaggc gatggccacc     480
ggctaaccct ggaagacatc ttccatgacc tgttctacca cttagagctc caggtcaacc     540
gcacctacca aatgcacctt ggagggaagc agagagaata tgagttcttc ggcctgaccc     600
ctgacacaga gttccttggc accatcatga tttgcgttcc cacctgggcc aaggagagtg     660 cccccctacat gtgccgagtg aagacactgc cagaccggac atggacctac tccttctccg     720
gagccttcct gttctccatg ggcttcctcg tcgcagtact ctgctacctg agctacagat     780
atgtcaccaa gccgccctgca cctcccaact ccctgaacgt ccagcgagtc ctgactttcc     840
```

```
agccgctgcg cttcatccag gagcacgtcc tgatccctgt ctttgacctc agcggcccca      900
gcagtctggc ccagcctgtc cagtactccc agatcagggt gtctggaccc agggagcccg      960
caggagctcc acagcggcat agcctgtccg agatcaccta cttagggcag ccagacatct     1020
ccatcctcca gccctccaac gtgccacctc cccagatcct ctccccactg tcctatgccc     1080
caaacgctgc ccctgaggtc gggcccccat cctatgcacc tcaggtgacc cccgaagctc     1140
aattcccatt ctacgcccca caggccatct ctaaggtcca gccttcctcc tatgcccctc     1200
aagccactcc ggacagctgg cctccctcct atggggtatg catggaaggt tctggcaaag     1260
actcccccac tgggacactt tctagtccta aacaccttag gcctaaaggt cagcttcaga     1320
aagagccacc agctggaagc tgcatgttag gtggcctttc tctgcaggag gtgacctcct     1380
tggctatgga ggaatcccaa gaagcaaaat cattgcacca gccctgggg atttgcacag      1440
acagaacatc tgacccaaat gtgctacaca gtggggagga agggacacca cagtacctaa     1500
agggccagct ccccctcctc tcctcagtcc agatcgaggg ccaccccatg tccctccctt     1560
tgcaacctcc ttccggtcca tgttcccct cggaccaagg tccaagtccc tggggcctgc      1620
tggagtccct tgtgtgtccc aaggatgaag ccaagagccc agcccctgag acctcagacc     1680
tggagcagcc cacagaactg gattctcttt tcagaggcct ggccctgact gtgcagtggg     1740
agtcctgagg ggaatgggaa aggcttggtg cttcctccct gtccctaccc agtgtcacat     1800
ccttggctgt caatcccatg cctgcccatg ccacacactc tgcgatctgg cctcagacgg     1860
gtgcccttga gagaagcaga gggagtggca tgcagggccc ctgccatggg tgcgctcctc     1920
accggaacaa agcagcatga taaggactgc agcggggag ctctggggag cagcttgtgt      1980
agacaagcgc gtgctcgctg agccctgcaa ggcagaaatg acagtgcaag gaggaaatgc     2040
agggaaactc ccgaggtcca gagccccacc tcctaacacc atggattcaa agtgctcagg     2100
gaatttgcct ctccttgccc cattcctggc cagtttcaca atctagctcg acagagcatg     2160
aggcccctgc ctcttctgtc attgttcaaa ggtgggaaga gagcctggaa aagaaccagg     2220
cctggaaaag aaccagaagg aggctgggca gaaccagaac aacctgcact tctgccaagg     2280
ccagggccag caggacggca ggactctagg gaggggtgtg gcctgcagct cattcccagc     2340
cagggcaact gcctgacgtt gcacgatttc agcttcattc ctctgataga acaaagcgaa     2400
atgcaggtcc accagggagg gagacacaca agccttttct gcaggcagga gtttcagacc     2460
ctatcctgag aatgggtttt gaaaggaagg tgagggctgt ggcccctgga cgggtacaat     2520
aacacactgt actgatgtca caactttgca agctctgcct tgggttcagc ccatctgggc     2580
tcaaattcca gcctcaccac tcacaagctg tgtgacttca aacaaatgaa atcagtgccc     2640
agaacctcgg tttcctcatc tgtaatgtgg ggatcataac acctacctca tggagttgtg     2700
gtgaagatga aatgaagtca tgtctttaaa gtgcttaata gtgcctggta catgggcagt     2760
gcccaataaa cggtagctat ttaaaaaaaa aaaaa                                2795
```

<210> SEQ ID NO 5
<211> LENGTH: 574
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 5

```
Met Arg Thr Leu Leu Thr Ile Leu Thr Val Gly Ser Leu Ala Ala His
 1               5                   10                  15
```

-continued

```
Ala Pro Glu Asp Pro Ser Asp Leu Leu Gln His Val Lys Phe Gln Ser
             20                  25                  30

Ser Asn Phe Glu Asn Ile Leu Thr Trp Asp Ser Gly Pro Glu Gly Thr
         35                  40                  45

Pro Asp Thr Val Tyr Ser Ile Glu Tyr Lys Thr Tyr Gly Glu Arg Asp
     50                  55                  60

Trp Val Ala Lys Lys Gly Cys Gln Arg Ile Thr Arg Lys Ser Cys Asn
 65                  70                  75                  80

Leu Thr Val Glu Thr Gly Asn Leu Thr Glu Leu Tyr Tyr Ala Arg Val
                 85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430
```

```
            Lys Glu Pro Pro Ala Gly Ser Cys Met Leu Gly Gly Leu Ser Leu Gln
                435                 440                 445

Glu Val Thr Ser Leu Ala Met Glu Glu Ser Gln Glu Ala Lys Ser Leu
                450                 455                 460

His Gln Pro Leu Gly Ile Cys Thr Asp Arg Thr Ser Asp Pro Asn Val
            465                 470                 475                 480

Leu His Ser Gly Glu Glu Gly Thr Pro Gln Tyr Leu Lys Gly Gln Leu
                            485                 490                 495

Pro Leu Leu Ser Ser Val Gln Ile Glu Gly His Pro Met Ser Leu Pro
                        500                 505                 510

Leu Gln Pro Pro Ser Gly Pro Cys Ser Pro Ser Asp Gln Gly Pro Ser
                    515                 520                 525

Pro Trp Gly Leu Leu Glu Ser Leu Val Cys Pro Lys Asp Glu Ala Lys
                530                 535                 540

Ser Pro Ala Pro Glu Thr Ser Asp Leu Glu Gln Pro Thr Glu Leu Asp
            545                 550                 555                 560

Ser Leu Phe Arg Gly Leu Ala Leu Thr Val Gln Trp Glu Ser
                            565                 570
```

<210> SEQ ID NO 6
<211> LENGTH: 3485
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 6

```
tccagctggg tagccggggg agcgcgcgtg ggggctccgc gagtcgctcg cccttggttt     60
ctggggaagc ctgggggacg cggctgtggc ggaggcgccc tgggactcag gtcgcctgga    120
gcgtggcacg cagagcccca ggcgcggagc tgaggccgcg cggccgcgct tggccccagc    180
gggcgtggga ctgagcagtc tgctgccccc cgacatgtga cccagccccg ccgcccatgc    240
gggctcccgg ccgcccggcc ctgcggccgc tgccgctgcc gccgctgctg ctgttgctcc    300
tggcggcgcc ttggggacgg gcagttccct gtgtctctgg tggtttgcct aaacctgcaa    360
acatcacctt cttatccatc aacatgaaga atgtcctaca atggactcca ccagagggtc    420
ttcaaggagt taaagttact tacactgtgc agtatttcat atatgggcaa aagaaatggc    480
tgaataaatc agaatgcaga aatatcaata gaacctactg tgatctttct gctgaaactt    540
ctgactacga caccagtat tatgccaaag ttaaggccat tgggggaaca aagtgttcca    600
aatgggctga agtggacgg ttctatcctt ttttagaaac acaaattggc ccaccagagg    660
tggcactgac tacagatgag aagtccattt ctgttgtcct gacagctcca gagaagtgga    720
agagaaatcc agaagacctt cctgtttcca tgcaacaaat atactccaat ctgaagtata    780
acgtgtctgt gttgaatact aaatcaaaca gaacgtggtc ccagtgtgtg accaaccaca    840
cgctggtgct cacctggctg gagccgaaca ctctttactg cgtacacgtg gagtccttcg    900
tcccagggcc ccctcgccgt gctcagcctt ctgagaagca gtgtgccagg actttgaaag    960
atcaatcatc agagttcaag gctaaaatca tcttctggta tgttttgccc atatctatta   1020 ccgtgttct tttttctgtg atgggctatt ccatctaccg atatatccac gttggcaaag   1080
agaaacaccc agcaaatttg attttgattt atggaaatga atttgacaaa agattctttg   1140
tgcctgctga aaaatcgtg attaacttta tcaccctcaa tatctcggat gattctaaaa   1200
tttctcatca ggatatgagt ttactgggaa aaagcagtga tgtatccagc cttaatgatc   1260
```

-continued

```
ctcagcccag cgggaacctg aggcccccct aggaggaaga ggaggtgaaa catttagggt    1320
atgcttcgca tttgatggaa atttttgtg actctgaaga aaacacggaa ggtacttctt     1380
tcacccagca agagtccctc agcagaacaa taccccgga taaaacagtc attgaatatg     1440
aatatgatgt cagaaccact gacatttgtg cggggcctga agagcaggag ctcagtttgc    1500
aggaggaggt gtccacacaa ggaacattat tggagtcgca ggcagcgttg gcagtcttgg    1560
gcccgcaaac gttacagtac tcatacaccc ctcagctcca agacttagac cccctggcgc    1620
aggagcacac agactcggag gaggggccgg aggaagagcc atcgacgacc ctggtcgact    1680
gggatcccca aactggcagg ctgtgtattc cttcgctgtc cagcttcgac caggattcag    1740
agggctgcga gccttctgag ggggatgggc tcggagagga gggtcttcta tctagactct    1800
atgaggagcc ggctccagac aggccaccag agaaaatga aacctatctc atgcaattca     1860
tggaggaatg ggggttatat gtgcagatgg aaaactgatg ccaacacttc cttttgcctt    1920
ttgtttcctg tgcaaacaag tgagtcaccc ctttgatccc agccataaag tacctgggat    1980
gaaagaagtt ttttccagtt tgtcagtgtc tgtgagaatt acttatttct tttctctatt    2040
ctcatagcac gtgtgtgatt ggttcatgca tgtaggtctc ttaacaatga tggtgggcct    2100
ctggagtcca ggggctggcc ggttgttcta tgcagagaaa gcagtcaata aatgtttgcc    2160
agactgggtg cagaatttat tcaggtgggt gtactctggc ctcttggttc attattttca    2220
aacaagcaca cttgtacaat tattttctgg gtacttccca tatgcacata gcactgtaaa    2280
aaatatttcc caaagatcac tcattttata aataccactt tttcagaatt gggtttattg    2340
cgagcaggag gagatactta aaacatgcac ataccaggt tggtggtaa gttggtcaca      2400
tgtgaaaacc tcaactattt aatcatcatg attcatattt tgagtgaata catcaggcac    2460
agaccttcat gatatcacac actcttggct actttaagag gccatcttta atactttatg    2520
agtagttctg gagtgtaaac ataaacgagt attcttttgt agtcagaaaa gtgtcctctc    2580
aataatttag tagggctta ttgtctctca aaactaacct aaaagaaaat gacacatttt     2640
ataatagaat attacattta tttctggaag tgtgttttca aaaagatatt tacatagtct    2700
gtaaactaga aagtgttagg taaagctcta ggttactgtg ttactattat aatattaaac    2760
attcgaatag gcagtcgttc aaagactctt tggaatatct atgaatgaat atcctctatt    2820
cttataatat taaaacccat aagtaaatat aggacataca agagaaatga gttaaatgac    2880
tatgtaaggg agagtttatt aaaatttgat gaaatttact gtaggaacta aactatgcca    2940
taaaacaata gctttctagt tcatttccag taactgttcc catctccttt accacttgtt    3000
aagaaaatta aattcttcag tcacgctgct ttaaaatggg acaaaatcta ttaagttgaa    3060
ccatatataa ttgtggatat ttggctgttt ttaatctgac aagcagtaac ttcatatggt    3120
ttgccttaat atatatttgt tttagtcatg aactctataat ccattgatgc tctttcatga   3180
gaagagatat gacccatatt tccttattga tattattggt acaggcagac aaccctggta    3240
ggagagatgg attctggggt catgaccttt cgtgattatc cgcaaatgca aacagtttca    3300
gatctaatgg tttaatttag ggagtaatta tattaatcag agtgttctgt tattctcaat    3360
ctttatagaa acgattctgc tggttttgaa gaacagatgt attacactaa ctgtaaaagt    3420
agttcaagag tgagaaagaa taaattgtta ttaagagcaa aagaaaaata aagtgattga    3480
tgata                                                                3485
```

<210> SEQ ID NO 7

<211> LENGTH: 553
<212> TYPE: PRT
<213> ORGANISM: Artificial Sequence
<220> FEATURE:
<223> OTHER INFORMATION: Description of Artificial Sequence; Note = Synthetic Construct

<400> SEQUENCE: 7

```
Met Arg Ala Pro Gly Arg Pro Ala Leu Arg Pro Leu Pro Leu Pro Pro
 1               5                  10                  15

Leu Leu Leu Leu Leu Ala Ala Pro Trp Gly Arg Ala Val Pro Cys
            20                  25                  30

Val Ser Gly Gly Leu Pro Lys Pro Ala Asn Ile Thr Phe Leu Ser Ile
         35                  40                  45

Asn Met Lys Asn Val Leu Gln Trp Thr Pro Pro Glu Gly Leu Gln Gly
 50                  55                  60

Val Lys Val Thr Tyr Thr Val Gln Tyr Phe Ile Tyr Gly Gln Lys Lys
 65                  70                  75                  80

Trp Leu Asn Lys Ser Glu Cys Arg Asn Ile Asn Arg Thr Tyr Cys Asp
                 85                  90                  95

Leu Ser Ala Glu Thr Ser Asp Tyr Glu His Gln Tyr Tyr Ala Lys Val
                100                 105                 110

Lys Ala Ile Trp Gly Thr Lys Cys Ser Lys Trp Ala Glu Ser Gly Arg
            115                 120                 125

Phe Tyr Pro Phe Leu Glu Thr Gln Ile Gly Pro Pro Glu Val Ala Leu
130                 135                 140

Thr Thr Asp Glu Lys Ser Ile Ser Val Val Leu Thr Ala Pro Glu Lys
145                 150                 155                 160

Trp Lys Arg Asn Pro Glu Asp Leu Pro Val Ser Met Gln Gln Ile Tyr
                165                 170                 175

Ser Asn Leu Lys Tyr Asn Val Ser Val Leu Asn Thr Lys Ser Asn Arg
            180                 185                 190

Thr Trp Ser Gln Cys Val Thr Asn His Thr Leu Val Leu Thr Trp Leu
        195                 200                 205

Glu Pro Asn Thr Leu Tyr Cys Val His Val Glu Ser Phe Val Pro Gly
210                 215                 220

Pro Pro Arg Arg Ala Gln Pro Ser Glu Lys Gln Cys Ala Arg Thr Leu
225                 230                 235                 240

Lys Asp Gln Ser Ser Glu Phe Lys Ala Lys Ile Ile Phe Trp Tyr Val
                245                 250                 255

Leu Pro Ile Ser Ile Thr Val Phe Leu Phe Ser Val Met Gly Tyr Ser
            260                 265                 270

Ile Tyr Arg Tyr Ile His Val Gly Lys Glu Lys His Pro Ala Asn Leu
        275                 280                 285

Ile Leu Ile Tyr Gly Asn Glu Phe Asp Lys Arg Phe Phe Val Pro Ala
290                 295                 300

Glu Lys Ile Val Ile Asn Phe Ile Thr Leu Asn Ile Ser Asp Asp Ser
305                 310                 315                 320

Lys Ile Ser His Gln Asp Met Ser Leu Leu Gly Lys Ser Ser Asp Val
                325                 330                 335

Ser Ser Leu Asn Asp Pro Gln Pro Ser Gly Asn Leu Arg Pro Pro Gln
            340                 345                 350

Glu Glu Glu Glu Val Lys His Leu Gly Tyr Ala Ser His Leu Met Glu
        355                 360                 365

Ile Phe Cys Asp Ser Glu Glu Asn Thr Glu Gly Thr Ser Phe Thr Gln
```

-continued 370             375             380
Gln Glu Ser Leu Ser Arg Thr Ile Pro Pro Asp Lys Thr Val Ile Glu
385                 390                 395                 400

Tyr Glu Tyr Asp Val Arg Thr Thr Asp Ile Cys Ala Gly Pro Glu Glu
                405                 410                 415

Gln Glu Leu Ser Leu Gln Glu Glu Val Ser Thr Gln Gly Thr Leu Leu
            420                 425                 430

Glu Ser Gln Ala Ala Leu Ala Val Leu Gly Pro Gln Thr Leu Gln Tyr
        435                 440                 445

Ser Tyr Thr Pro Gln Leu Gln Asp Leu Asp Pro Leu Ala Gln Glu His
    450                 455                 460

Thr Asp Ser Glu Glu Gly Pro Glu Glu Pro Ser Thr Thr Leu Val
465                 470                 475                 480

Asp Trp Asp Pro Gln Thr Gly Arg Leu Cys Ile Pro Ser Leu Ser Ser
                485                 490                 495

Phe Asp Gln Asp Ser Glu Gly Cys Glu Pro Ser Glu Gly Asp Gly Leu
            500                 505                 510

Gly Glu Glu Gly Leu Leu Ser Arg Leu Tyr Glu Glu Pro Ala Pro Asp
        515                 520                 525

Arg Pro Pro Gly Glu Asn Glu Thr Tyr Leu Met Gln Phe Met Glu Glu
    530                 535                 540

Trp Gly Leu Tyr Val Gln Met Glu Asn
545                 550

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 8
tgcaaagcct gtggacttta gccaggtatc ag                            32

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 9
ccgcctgtgt gcactgtctc tgatg                                    25

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 10
atgtatttcc cagaaa                                              16

<210> SEQ ID NO 11
<211> LENGTH: 17
<212> TYPE: DNA
<213> ORGANISM: Artificial Sequence

```
<220> FEATURE:
<223> OTHER INFORMATION: Description of Artificial Sequence; Note =
      Synthetic Construct

<400> SEQUENCE: 11
ccttttctgg gaaatac                                                    17

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence; Note =
      Synthetic Construct

<400> SEQUENCE: 12
tgcaaagcct gtggacttta gccag                                           25
```